US012683000B2

(12) United States Patent
Yazdavar et al.

(10) Patent No.: US 12,683,000 B2
(45) Date of Patent: Jul. 14, 2026

(54) SYSTEMS AND METHODS FOR GENERATING PERSONALIZED CARE PATHS FOR PATIENTS

(71) Applicant: Optum, Inc., Minnetonka, MN (US)

(72) Inventors: Amirhossein Yazdavar, Scottsdale, AZ (US); David S. Monaghan, Dublin (IE); Jeremiah L. Tanner, Bettendorf, IA (US); Brian Carter, Dublin (IE); Andrew J. Plesniak, Mars, PA (US)

(73) Assignee: Optum, Inc., Minnetonka, MN (US)

( * ) Notice: Subject to any disclaimer, the term of this patent is extended or adjusted under 35 U.S.C. 154(b) by 340 days.

(21) Appl. No.: 18/153,625

(22) Filed: Jan. 12, 2023

(65) Prior Publication Data

US 2024/0242802 A1 Jul. 18, 2024

(51) Int. Cl.
*G16H 20/00* (2018.01)
*G16H 10/60* (2018.01)
*G16H 50/30* (2018.01)
*G16H 80/00* (2018.01)

(52) U.S. Cl.
CPC .............. *G16H 20/00* (2018.01); *G16H 10/60* (2018.01); *G16H 50/30* (2018.01); *G16H 80/00* (2018.01)

(58) Field of Classification Search
CPC ........ G16H 20/00; G16H 10/60; G16H 50/30; G16H 80/00
USPC .......................................................... 705/2
See application file for complete search history.

(56) References Cited

U.S. PATENT DOCUMENTS

| | | | |
|---|---|---|---|
| 10,902,944 B1 | 1/2021 | Casey et al. | |
| 11,177,025 B2 | 11/2021 | Bettencourt-Silva et al. | |
| 2011/0301977 A1 | 12/2011 | Belcher et al. | |
| 2012/0078651 A1 | 3/2012 | Henderson et al. | |
| 2012/0271612 A1 | 10/2012 | Barsoum et al. | |
| 2015/0339602 A1* | 11/2015 | Schlosser ............... | G06Q 10/10 705/3 |
| 2018/0089385 A1 | 3/2018 | Gupta et al. | |

(Continued)

OTHER PUBLICATIONS

Fouladvand, S., Gomez, F. R., Nilforoshan, H., Schwede, M., Noshad, M., Jee, O., . . . & Chen, J. (2022). Graph-based clinical recommender: Predicting specialists procedure orders using graph representation learning. Journal of Biomedical Informatics, 143, 104407. (Year: 2022).*

(Continued)

*Primary Examiner* — Winston R Furtado
(74) *Attorney, Agent, or Firm* — Bookoff McAndrews, PLLC

(57) ABSTRACT

Systems and methods are disclosed for generating a personalized care path for a patient. The method includes receiving, by one or more processors, relevant data associated with the patient from a plurality of data sources. The relevant data includes demographic data and medical data associated with the patient. The one or more processors using a graph convolutional neural network-based model determine the personalized care path for the patient based on the relevant data associated with the patient. The graph convolutional neural network-based model is trained based on a plurality of care paths of a plurality of patients represented by a patient-bucket-procedure (PBP) graph. The one or more processors provide data associated with the determined personalized care path for the patient to a device associated with a user.

20 Claims, 11 Drawing Sheets

(56) References Cited

U.S. PATENT DOCUMENTS

| | | | |
|---|---|---|---|
| 2019/0030370 A1* | 1/2019 | Hibbard | ............... A61N 5/1067 |
| 2020/0027531 A1* | 1/2020 | White | .................... G06F 40/30 |
| 2021/0202076 A1 | 7/2021 | Cheung | |

OTHER PUBLICATIONS

Ng, K., Kartoun, U., Stavropoulos, H., Zambrano, J. A., & Tang, P. C. (2021). Personalized treatment options for chronic diseases using precision cohort analytics. Scientific reports, 11(1), 1139. (Year: 2021).*

Alexandrou, D. A., Skitsas, I. E., & Mentzas, G. N. (2010). A holistic environment for the design and execution of self-adaptive clinical pathways. IEEE Transactions on Information Technology in Biomedicine, 15(1), 108-118. Retrieved from https://web.archive. org/web/20170829014412id_/http://imu.ntua.gr/sites/default/files/ biblio/Papers/a-holistic-environment-for-the-design-and-execution-of-self-adaptive-clinical-pathways.pdf. 11 pages.

Rajkomar, A., Oren, E., Chen, K., Dai, A. M., Hajaj, N., Hardt, M., . . . & Dean, J. (2018). Scalable and accurate deep earning with electronic health records. NPJ digital medicine, 1(1), 1-10. Retrieved from https://www.nature.com/articles/s41746-018-0029-1%22. 10 pages.

Sun, H., Amdt, D., De Roo, J., & Mannens, E. (2021). Predicting future state for adaptive clinical pathway management. Journal of biomedical informatics, 117, 103750. Retrieved from https://reader. elsevier.com/reader/sd/pii/S1532046421000794. 11 pages.

Sun, H., Depraetere, K., De Roo, J., Mels, G., De Vloed, B., Twagirumukiza, M., & Colaert, D. (2015). Semantic processing of EHR data for clinical research. Journal of biomedical informatics, 58, 247-259. Retrieved from https://reader.elsevier.com/reader/sd/ pii/S1532046415002312. 13 pages.

Verborgh, R., Arndt, D., Van Hoecke, S., De Roo, J., Mels, G., Steiner, T., & Gabarro, J. (2017). The pragmatic proof: Hypermedia API composition and execution. Theory and Practice of Logic Programming, 17(1), 1-48. Retrieved from https://arxiv.org/pdf/ 1512.07780.pdf. 47 pages.

Wang, H. Q., Li, J. S., Zhang, Y. F., Suzuki, M., & Araki, K. (2013). Creating personalised clinical pathways by semantic interoperability with electronic health records. Artificial intelligence in medicine, 58(2), 81-89.

* cited by examiner

SYSTEMS AND METHODS FOR GENERATING PERSONALIZED CARE PATHS FOR PATIENTS

TECHNICAL FIELD

The present disclosure relates generally to data processing for facilitating patient care plans, and more particularly, to systems and methods for generating personalized care paths for improved patient care.

BACKGROUND

Medical care paths may be utilized to manage quality in healthcare by providing standardization to care processes. However, due to a large number of possible variables for the treatment of patients, determining the most effective care path for an individual patient is challenging. Typically, care paths are manually compiled, e.g., by clinicians or medical directors, and are expensive and time-consuming to create, clinically validate, and maintain. Patients often request an episode-of-care (EoC), i.e., an individual care path, to comprehend the treatments being received and estimate the cost of the treatments. However, the recommended care paths are often too generic, and the EoC experienced by the patient may significantly deviate from the recommended care paths. Consequently, patients can be less inclined to trust recommended care path and thus fail to fully engage in the recommended care path to the detriment of their health.

At present, the conventional method for generating care paths rely on human experts. Such an approach is inefficient, error-prone, costly, and does not account for real-time changes in relevant data associated with the patients, e.g., real-time changes in the health condition of the patient that significantly impacts the prescribed care paths. In addition, the recommended care paths are not customized to the patient's requirements; rather a generic care path is proposed, hence patients often experience EoC that is different from the treatments proposed in the generic care path. Furthermore, service providers, e.g., healthcare service providers, have at their disposal vast amounts of data through the utilization of several healthcare information systems, but they are technically challenged to process, extract, and integrate the relevant data into the care path decision-making process to generate a personalized care path to the patients.

Unless otherwise indicated herein, the materials described in this section are not prior art to the claims in this application and are not admitted to be prior art, or suggestions of the prior art, by inclusion in this section.

SUMMARY

The present disclosure solves this problem and/or other problems described above or elsewhere in the present disclosure. The present disclosure teaches systems and methods for predicting an optimized care path for the patient using machine learning. In some embodiments, the present disclosure builds a patient-bucket-procedure (PBP) graph that identifies the intent of a sequence of procedures, e.g., medical procedures, in a bucket while modeling the semantics of their current procedural terminology (CPT) codes to generate a personalized care path. The methods and system also facilitate the management of care paths more systematically by enabling the care paths to be customized based on real-time processing of relevant data associated with the patients.

In some embodiments, a computer-implemented method for generating a personalized care path for a patient is disclosed. The computer-implemented method includes receiving, by one or more processors, relevant data associated with a patient from a plurality of data sources, wherein the relevant data includes demographic data and medical data associated with the patient; determining, by the one or more processors and using a graph convolutional neural network-based model, a personalized care path for the patient based on the relevant data associated with the patient, wherein the graph convolutional neural network-based model is trained based on a plurality of care paths of a plurality of patients represented by a patient-bucket-procedure (PBP) graph; and providing, by the one or more processors, data associated with the determined personalized care path for the patient to a device associated with a user.

In some embodiments, a system for generating a personalized care path for a patient is disclosed. The system includes one or more processors, and at least one non-transitory computer readable medium storing instructions which, when executed by the one or more processors, cause the one or more processors to perform operations including: receiving relevant data associated with the patient from a plurality of data sources, wherein the relevant data includes demographic data and medical data associated with the patient; determining, using a graph convolutional neural network-based model, the personalized care path for the patient based on the relevant data associated with the patient, wherein the graph convolutional neural network-based model is trained based on a plurality of care paths of a plurality of patients represented by a patient-bucket-procedure (PBP) graph; and providing data associated with the determined personalized care path for the patient to a device associated with a user.

In some embodiments, a non-transitory computer readable medium for generating a personalized care path for a patient is disclosed. The non-transitory computer readable medium stores instructions which, when executed by one or more processors, cause the one or more processors to perform operations including: receiving relevant data associated with the patient from a plurality of data sources, wherein the relevant data includes demographic data and medical data associated with the patient; determining, using a graph convolutional neural network-based model, the personalized care path for the patient based on the relevant data associated with the patient, wherein the graph convolutional neural network-based model is trained based on a plurality of care paths of a plurality of patients represented by a patient-bucket-procedure (PBP) graph; and providing data associated with the determined personalized care path for the patient to a device associated with a user.

It is to be understood that both the foregoing general description and the following detailed description are example and explanatory only and are not restrictive of the detailed embodiments, as claimed.

BRIEF DESCRIPTION OF THE DRAWINGS

The accompanying drawings, which are incorporated in and constitute a part of this specification, illustrate various example embodiments and together with the description, serve to explain the principles of the disclosed embodiments.

DETAILED DESCRIPTION

Figure 1:
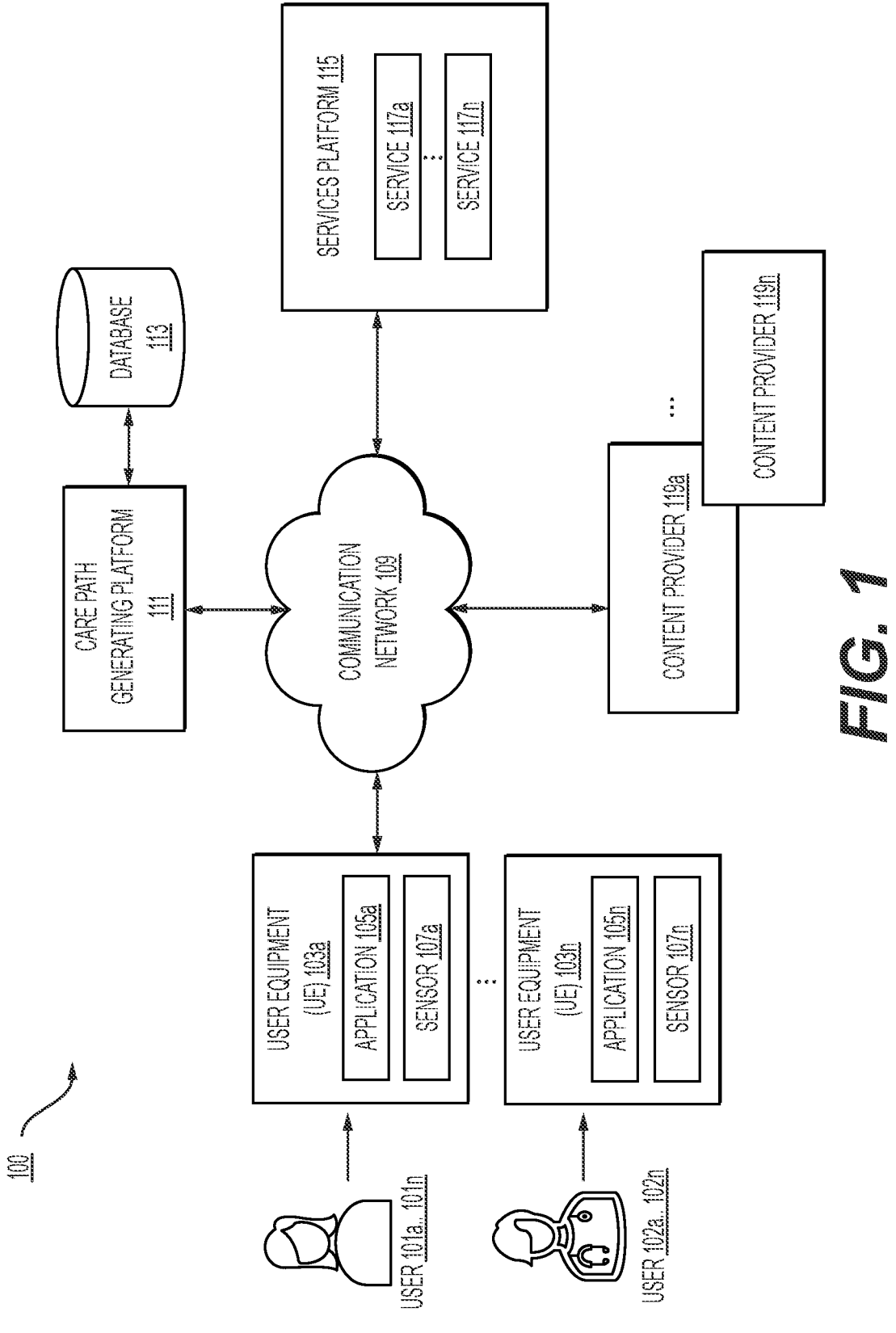
FIG. 1 is a diagram showing an example of a system that is capable of generating personalized care paths for patients, according to some embodiments of the disclosure.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

Various non-limiting embodiments of the present disclosure will now be described to provide an overall understanding of the principles of the structure, function, and use of systems and methods disclosed herein for modeling and generating individualized personal medical care paths for patients.

A medical care path is a collection of medical and management activities, carried out over a period of time, as part of a patient's medical treatment plan. The personalized care path that a patient experiences is referred to as an episode of care (EoC), and is defined as a set of services, e.g., medical treatments or procedures, provided to the patient to treat a clinical condition. Patients often query the service providers, e.g., hospitals, clinics, or insurance companies, for EoC to be aware of the treatments they are administered and get an estimate of the treatment's cost. Conventional methods for generating care paths are highly reliant on human domain expertise and involve clinicians and medical directors. Such methods are costly, time-consuming, and due to their inability to consider the contextual information of individual patients, a median care path is provided to the patients. The median care paths are often too generic, and do not reflect the actual sequence of treatments the patient experiences.

Each patient has individual requirements, medical histories, and distinct circumstances that contribute to a unique EoC for the same procedure. For example, patients often experience EoC that significantly deviates from the recommended care path because of their unique circumstances. Hence, prescribing a generic care path that differs from the EoC experienced by the patient is inaccurate and unreliable. An accurate prediction of personalized EoC for each patient is desired. To that end, it is important to develop a tailored care path generator system that obtains contextual information about patients from various data sources. Furthermore, there is a scarcity of widely accepted datasets that are integrated with the patients' profiles in the care path generation domain. There is a need to create a platform that integrates background knowledge from various domains with patient information.

Despite the increasing availability of medical information from various sources, utilizing it for medical advice comes with a risk of mistreatment or misunderstanding. The health system is technically challenged to implement a method that accurately evaluates the available medical information to generate tailored care paths for patients, facilitate the management of care paths in a more systematic manner, and/or enable care paths to be modified based on patients' contextual information. The health system is further technically challenged in extracting relevant knowledge from the available medical information from various sources to help in the decision-making process of generating personalized care paths for patients.

To address these challenges, a system 100 of FIG. 1 introduces the capability to generate personalized care paths by employing relevant data from various data sources, e.g., healthcare graph data source, with graph-based neural networks. While prior solutions to generate care paths mostly relied on human intelligence, the system 100 describes a data-driven approach that leverages artificial intelligence (AI) technologies, e.g., graph convolutional neural network and healthcare graph data, to integrate heterogonous signals for recommending personalized care paths to patients.

In one embodiment, the system 100 integrates relevant data, e.g., integrating patient data with existing relevant cost-related signals, extracted from a plurality of data sources, e.g., a database 113 and a content provider 119, while recommending a personalized care path to a patient. The system 100 builds a patient-bucket-procedure (PBP) graph where a bucket of CPT codes represents the intent of the care path while modeling the semantics of CPT codes, and uses the PBP graph to generate a personalized care path. For example, the system 100 contextualizes the sequence of CPT codes by predefined time intervals and semantic representation of the code's description. The system 100 formulates the care path generator problem as a link prediction problem while incorporating heterogonous signals by one or more aggregators. For example, the graph-based neural network aggregates heterogonous patient signals for recommending a care path.

FIG. 1 introduces a capability to implement modern communication and data processing capabilities into methods and systems for generating a personalized care path for a patient. FIG. 1, an example architecture of one or more example embodiments of the present invention, includes a system 100 that comprises users 101*a*-101*n* (collectively referred to as user 101), users 102*a*-102*n* (collectively referred to as a user 102), user equipment (UE) 103*a*-103*n*

(collectively referred to as UE 103) that includes applications 105a-105n (collectively referred to as an application 105) and sensors 107a-107n (collectively referred to as a sensor 107), a communication network 109, a care path generating platform 111, a database 113, a services platform 115 that includes services 117a-117n (collectively referred to as a service 117), and content providers 119a-119n (collectively referred to as a content provider 119).

In one embodiment, the user 101 is a person or a group of people interacting with a user interface or a web interface of the UE 103 to access a service, e.g., a care path generating service or any other healthcare service. In one example embodiment, user 101 includes a registered patient, a potential patient, a returning patient, a visiting patient, and/or any other authorized user of the service that provides contextual information to request or access a personalized care path. In one example embodiment, the user 101 shares general health-related information, e.g., blood pressure, body temperature, skin temperature, heart rate variability, heart rate, breathing rate, blood glucose level, oxygen saturation, stress levels, etc. In another example embodiment, the user 101 shares specialized health indicators, e.g., lab data, blood indicators, physiological data, weight data, etc. In a further example embodiment, the user 101 shares demographic data, location information, preference information, and/or any other relevant information.

In one embodiment, the user 102 is a service provider, e.g., physicians, surgeons, or any other healthcare professional, that provides medical-related services to patients, e.g., the user 101. In one example embodiment, the user 102 has access to hospital information system computing device(s) that include electronic health record (EHR) computing devices, admission, discharge, transfer (ADT) system computing devices, registration and billing system computing devices, clinical information system computing devices, hospital resource management system computing devices, and so forth. The user 102 shares medical records, medical history, medication charts, medical intake information, claim data, and other health-related information associated with the user 101. In another example embodiment, the user 102, via the system 100, assists in tailoring a care path for a specific user by reviewing the prescribed care path and recommending an adjustment based on the available medical information associated with the specific user. In a further example embodiment, the user 102, via the system 100, monitors, regularly or per schedule, the prescribed care paths for any anomalies, and such anomalies are promptly addressed by changing the patient's treatment plan.

In one embodiment, the UE 103 includes, but is not restricted to, any type of mobile terminal, wireless terminal, fixed terminal, or portable terminal. Examples of the UE 103, include, but are not restricted to, a mobile handset, a wireless communication device, a station, a unit, a device, a multimedia computer, a multimedia tablet, an Internet node, a communicator, a desktop computer, a laptop computer, a notebook computer, a netbook computer, a tablet computer, a Personal Communication System (PCS) device, a personal navigation device, a Personal Digital Assistant (PDA), a digital camera/camcorder, an infotainment system, a dashboard computer, a television device, or any combination thereof, including the accessories and peripherals of these devices, or any combination thereof. In addition, the UE 103 facilitates various input means for receiving and generating information, including, but not restricted to, a touch screen capability, a keyboard, and keypad data entry, a voice-based input mechanism, and the like. Any known and future implementations of the UE 103 are also applicable.

In one embodiment, the applications 105 includes various applications such as, but not restricted to, content provisioning applications, software applications, networking applications, multimedia applications, media player applications, camera/imaging applications, and the like. In one embodiment, one of the applications 105 at the UE 103 acts as a client for care path generating platform 111 and performs one or more functions associated with the functions of the care path generating platform 111 by interacting with the care path generating platform 111 over the communication network 109.

By way of example, each sensor 107 includes any type of sensor. In one embodiment, the sensors 107 include, for example, a network detection sensor for detecting wireless signals or receivers for different short-range communications (e.g., Bluetooth, Wi-Fi, Li-Fi, near field communication (NFC), etc.), a global positioning sensor for gathering location data, a camera/imaging sensor for gathering image data, an audio recorder for gathering audio data, and the like. In another embodiment, the sensors 107 are provided in wearable devices and/or any health monitoring devices, that captures parameter such as health data, e.g., activity data, vitals data, and any other data indicative of the user's health condition, eating/drinking patterns, exercise regime, medication intake, age, weight, gender, etc., of the user 101. In another embodiment, the sensors 107 include, for example, inertial measurement unit (IMU) sensors, electrocardiogram (ECG) sensors, sensors to detect blood glucose level, sensors to measure respiration rate, heart rate detection sensors, sensor to monitor body temperature, micro-electro-mechanical system (MEMS) based miniature motion sensors, gyroscope, accelerometer, magnetometer, infrared sensor, microphone, gas sensor, etc.

In one embodiment, various elements of the system 100 communicate with each other through the communication network 109. The communication network 109 supports a variety of different communication protocols and communication techniques. In one embodiment, the communication network 109 allows the care path generating platform 111 to communicate with the UE 103, the services platform 115, and the content provider 119. The communication network 109 of the system 100 includes one or more networks such as a data network, a wireless network, a telephony network, or any combination thereof. It is contemplated that the data network is any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network is, for example, a cellular communication network and employs various technologies including 5G (5th Generation), 4G, 3G, 2G, Long Term Evolution (LTE), wireless fidelity (Wi-Fi), Bluetooth®, Internet Protocol (IP) data casting, satellite, mobile ad-hoc network (MANET), vehicle controller area network (CAN bus), and the like, or any combination thereof.

In one embodiment, the care path generating platform 111 is a platform with multiple interconnected components. The care path generating platform 111 includes one or more servers, intelligent networking devices, computing devices, components, and corresponding software for generating a personalized care path for a patient. In addition, it is noted that the care path generating platform 111 may be a separate entity of the system 100.

In one embodiment, the care path generating platform 111 analyzes one or more requirements of the patient, e.g., understanding the requirements of corresponding applications to determine the characteristics of the patient's data. In one embodiment, the care path generating platform 111 collects relevant data associated with the patient from a plurality of data sources and integrates the relevant data into the care path to customize the care path for the patient. In one example embodiment, relevant data include patient characteristics data, claim characteristics data, provider characteristics data, treatment characteristics data, and/or healthcare graphs, e.g., diagnosis codes, medication codes, lab test codes, and/or medical code descriptions associated with the patient.

In one embodiment, the care path generating platform 111 iteratively analyzes care path patterns of a plurality of patients, via a graph convolutional neural network-based model trained by a PBP graph, for modeling a care path for a patient. The PBP graph represents the interaction between each patient, at least one bucket, and/or at least one medical procedure. The PBP graph has two main components, including the embedding layer and the heterogeneous aggregators for patients, buckets, and procedures, respectively. In one embodiment, the care path generating platform 111 collects a sequence of CPT codes into one or more buckets based, at least in part, on their time of occurrence and/or their semantics information. The intent of one or more buckets is modeled based, at least in part, on patient item collaborative filtering that models the semantic information of the CPT codes and personal procedures of the patient, and multi-item CPT code correlations indicating a specific care path for the patient. In one embodiment, the intent of one or more buckets indicates the purpose for collecting and/or correlating the CPT codes, e.g., care pathways to treat a particular disease or perform a specific surgical procedure. The care path generating platform 111 generates the PBP graph based, at least in part, on one or more buckets with the collection of the CPT codes, wherein bucket nodes are incorporated to represent semantics information of the care paths of the patients.

In one embodiment, the care path generating platform 111 models the care path to predict interactions over the PBP graph while designing heterogeneous aggregators that learn the embedding of each node. Heterogeneity comes from multi-type signals that impact the modeling of the patient's care path and/or cost. The care path generating platform 111 introduces heterogeneous interactions on the PBP graph, wherein certain interactive layers model the patient-procedure signal, the bucket-procedure signal, and the patient-bucket interactive signal. In one embodiment, the care path generating platform 111 builds three separate interaction matrices from the PBP graph, including a patient-bucket interaction matrix ($R_{pb}$), a bucket-CPT interaction matrix ($R_{bc}$), and a patient-CPT interaction matrix ($R_{pc}$).

In one embodiment, the care path generating platform 111 categorizes the care path into a plurality of segments (e.g., buckets) based, at least in part, on treatment characteristics and pre-defined time of occurrence of the treatment characteristics within the care path. In one embodiment, the care path generating platform 111 contextualizes a sequence of CPT codes based, at least in part, on the time of occurrence and/or semantics information. The semantics information is generated via certain natural language processing (NLP) methods. In another embodiment, the care path generating platform 111 collects and integrates, via a graph convolutional neural network-based model, embeddings of nodes associated with patients with similar health and/or medical characteristics to generate an accurate care path for the patient.

In one embodiment, the care path generating platform 111 aggregates certain neighbor information, e.g., corresponding buckets, CPT codes associated with the corresponding buckets, patients with similar health profiles, etc., to model collaborative filtering signals in the PBP graph by constructing and then aggregating messages over the graph. For example, the care path generating platform 111 defines a bucket aggregator that summarizes the multi-item correlation inside the corresponding buckets and combines it with the associated patient. In another embodiment, the care path generating platform 111 collects and integrates, via the graph convolutional neural network-based model trained based on the PBP graph, embeddings of nodes, e.g., bucket nodes and CPT nodes, associated with one or more patients with similar characteristics to improve the accuracy of the personalized care paths. For example, the aggregators of the graph convolutional neural network-based model collectively aggregate the embeddings of the nodes from both the neighborhood as well as other patients, e.g., non-neighborhood patients that are not element of the set of neighborhood patients, in the dataset and use the learned representation to recommend care paths to patients.

In one embodiment, the care path generating platform 111 compares the care path with an existing rule-based legacy care path generator to validate the correctness of the predicted care path. The comparison includes analyzing the performance of the suggested framework of the care path. In addition, the output, e.g., a care path, is evaluated by machine-learning based evaluation criteria using train-validation-test datasets.

There are costs associated with each treatment option. Depending on the patient's budget, certain treatment options may be more reasonable. In one embodiment, the care path generating platform 111 integrates computer programs, e.g., a treatment cost estimator, to determine cost estimates for one or more treatments in the care path. The care path generating platform 111 optimizes the care path by selecting one or more treatment options based on the cost estimate. In one example embodiment, the cost estimate is based on average costs calculated from claim information, geographic averages, fee schedules of the service provider, etc. It is understood, however, that the cost estimate may be based on any other relevant data sources or a combination of sources.

In one embodiment, the database 113 accesses or includes any suitable data that may be used to generate one or more care paths or portions thereof. Specifically, embodiments of the present disclosure include databases with data related to one or more patients including medical coverage, medical conditions, medical history, etc.; databases with data related to one or more health plans including coverage amounts, deductibles, coinsurance, copays, etc.; databases with data related to treatment including treatment options for particular conditions, illnesses and/or health states, etc.; databases with data related to cost data including cost of services by treatment, cost of services by the provider, cost of services by location or geography, etc.; databases with data related to provider selection including provider's cost, provider's quality, provider outcomes data, and/or consumer feedback. It is understood that any other suitable data may be included.

In one embodiment, the database 113 is any type of database, such as relational, hierarchical, object-oriented, and/or the like, wherein data are organized in any suitable manner, including data tables or lookup tables. In one embodiment, the database 113 stores content associated with the UE 103, the care path generating platform 111, and the services 117 of the services platform 115, and manages multiple types of information that provide means for aiding in the content provisioning and sharing process. In one embodiment, the database 113 includes a machine-learning based training database with a pre-defined mapping defining a relationship between various input parameters and output parameters based on various statistical methods. For example, the training database includes machine-learning algorithms to learn mappings between input parameters related to the patients, e.g., physiological parameters, user's health records, user's lifestyle patterns, etc., and inputs provided by the medical experts, e.g., medical records. In one embodiment, the training database includes a dataset that includes data collections that are not subject-specific, e.g., data collections based on population-wide observations, local, regional or super-regional observations, treatment-based observations, diagnosis-based observations, and the like. Example datasets include care path data, demographic data, pharmacy data, insurance data, drug interaction information, market data, encyclopedias, scientific and medical-related periodicals and journals, research studies data, scientifically-curated genetics-related information, nutritional data, exercise data, physician and hospital/clinic location information, physician billing information, physician reimbursement information, and the like. In an embodiment, the training database is routinely updated and/or supplemented based on machine learning methods.

The services platform 115 includes any type of service. By way of example, the services platform 115 includes content (e.g., audio, video, images, etc.) provisioning services, application services, storage services, contextual information determination services, location-based services, notification services, social networking services, etc. In one embodiment, the services platform 115 interacts with the UE 103, the care path generating platform 111, and the content provider 119 to supplement or aid in the processing of the content information. In one embodiment, the services platform 115 is implemented or embedded in the care path generating platform 111 or in its functions. In one example embodiment, the services platform 115 assists the care path generating platform 111 in accessing user account information from social networks and retrieve social network activity data, e.g., user's lifestyle data.

By way of example, the services 117 is an online service that reflects the interests and/or activities of the user 101. The services 117 share user profile information, activity information, contextual information, historical user information and interests, and/or location information, and provides for data portability. In one example embodiment, the services 117 assist in providing the care path generating platform 111 with health-related information, e.g., activity information that affects the health conditions of the users, contextual information that affects the recommended care path for the users, and a variety of additional information.

In one embodiment, the content provider 119 provides certain content to the UE 103, the care path generating platform 111, and the services 117 of the services platform 115. The content provided is any type of content, such as image content (e.g., pictures), textual content, audio content, video content, etc., from various data sources, e.g., CPT code databases, medical records databases, a regulation database, e.g., state or federal managed database, and/or any third-party databases. In another embodiment, the content provider 119 manage access to a central repository of data and offer a consistent, standard interface to data.

By way of example, the UE 103, the care path generating platform 111, the services platform 115, and the content provider 119 communicate with each other and other components of the communication network 109 using well known, new or still developing protocols. In this context, a protocol includes a set of rules defining how the network nodes within the communication network 109 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers as defined by the OSI Reference Model.

Figure 2:
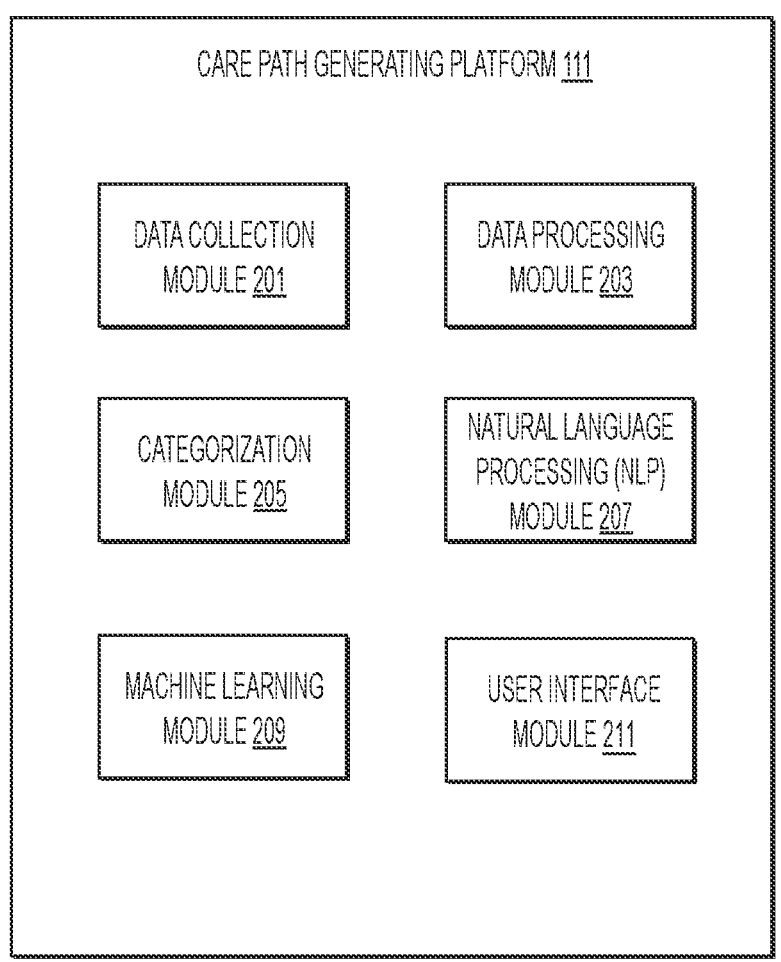
FIG. 2 is a diagram of the components of a care path generating platform, according to some embodiments of the disclosure.

FIG. 2 is a diagram of the components of the care path generating platform 111, according to some aspects of the disclosure. As used herein, terms such as "component" or "module" generally encompass hardware and/or software, e.g., that a processor or the like is used to implement associated functionality. By way of example, the care path generating platform 111 includes one or more components for generating a personalized care path for a patient. It is contemplated that the functions of these components are combined in one or more components or performed by other components of equivalent functionality. In one embodiment, the care path generating platform 111 comprises a data collection module 201, a data processing module 203, a categorization module 205, a natural language processing (NLP) module 207, a machine learning module 209, a user interface module 211, or any combination thereof.

In one embodiment, the data collection module 201 collects relevant data, e.g., patient characteristics data, claim characteristics data, provider characteristics data, and/or treatment characteristics data, etc., associated with the user 101 through various data collection techniques. In one embodiment, the data collection module 201 uses a web-crawling component to access various databases, e.g., the database 113, or other information sources, e.g., the content provider 119, to collect relevant data associated with the user 101. In one embodiment, the data collection module 201 includes various software applications, e.g., data mining applications in Extended Meta Language (XML), that automatically search for and return relevant data regarding the user 101. In another embodiment, the data collection module 201 collects health data associated with the user 101 via a variety of the UE 103, e.g., monitoring devices that measures the physiological parameters, e.g., heart rate, blood oxygen saturation levels, respiratory rate, glucose level, blood pressure, weight, etc., of the user 101. In one example embodiment, the UE 103 includes a smartwatch, a smart wristband, a smartphone, smart clothing, or other devices including the sensors 107, e.g., a gyroscope, an accelerometer, a magnetometer, an infrared sensor, a camera, a microphone, a photo-detector, etc., capable of capturing activity data and vital data of user 101. In one embodiment, these monitoring devices are equipped with operating systems like Android™, iOS™, Windows®, Linux™ OS, or hybrid frameworks that enable efficient integration. In one example embodiment, the collection of relevant data is automated, e.g., an automatic human activity recognition technique that captures data from wearable and/or non-wearable monitoring devices. The human activity recognition technique is used to build Human Activity Recognition (HAR) datasets.

In one embodiment, the data processing module 203 processes, parses, and arranges data collected by the data collection module 201 into a common format that is easily processed by other modules and platforms. In one example embodiment, the data processing module 203 processes health-related data of the user 101, e.g., blood pressure, body temperature, heart rate variability, heart rate, resting heart rate, breathing rate, blood glucose, oxygen saturation, or stress levels, to determine changing health conditions of the user 101. In another example embodiment, the data processing module 203 processes the activity data of the user 101 to determine their lifestyle patterns, e.g., eating patterns, drinking patterns, sleeping patterns, exercise patterns, and other activity data such as smoking, drinking, etc. In one embodiment, the data processing module 203 performs various calculations on the processed data to determine health scores for the user 101, wherein patients with lower health scores are prioritized over patients with higher health scores while generating the care paths. In one embodiment, the data processing module 203 performs various calculations on the processed data to determine adherence scores based, at least in part, on adherence to the prescribed care paths by the user 101. In one embodiment, the data processing module 203 performs various calculations on the processed data to determine a risk score that indicates the recent health condition of the user 101 and adjusts the care path, in real-time or near real-time, based on the recent health condition.

In one embodiment, the categorization module 205 monitors, in real-time or near real-time, care paths associated with a plurality of patients. The categorization module 205 then categorizes the monitored care paths associated with the plurality of patients based, at least in part, on their characteristics, e.g., care paths for performing a particular surgical procedure, e.g., lumbar fusion, are grouped in the same category. In another embodiment, the categorization module 205 categorizes the CPT codes within each of the grouped care paths. For example, the medical treatments or medical procedures for lumbar fusion typically include initial diagnosis, medication, laboratory results, hospitalization, medical procedures, rehabilitation, etc. Such categorization of CPT codes shows the frequency of occurrence of the medical treatments or medical procedures in the care path for lumbar fusion. In another embodiment, the categorization module 205 categorizes the CPT codes based, at least in part, on their time of occurrence within the care path. A co-occurrence of CPT codes within a specific time period shows latent relations between the CPT codes, e.g., treatment often begins with an initial consultation followed by blood draws, laboratory tests, and physician evaluation. In another embodiment, the categorization module 205 categorizes the care paths based, at least in part, on their cost, e.g., an expensive medical treatment in the care path can be replaced with a cheaper alternative based on the income level of the patient and/or insurance coverage. Analysis of such categorized data by one or more modules of the care path generating platform 111 can lead to greater efficiency, better decision-making, improved patient care, and lower costs.

In one embodiment, the NLP module 207 evaluates care paths associated with the plurality of patients to build a semantic relationship between the CPT codes. The NLP module 207 utilizes one or more language modeling techniques, e.g., statistical models, neural-network models, transformers models, etc., to build semantic relationships between the CPT codes of the care path. In one example embodiment, CPT codes describe tests, surgeries, evaluations, and any other medical procedure performed by a healthcare provider on a patient. A CPT code set is large and includes descriptions and codes for numerous medical procedures, and the NLP module 207 analyzes the descriptions and codes in the CPT code set to build a semantic relationship between the CPT codes. In one embodiment, the NLP module 207 trains a machine learning model to contextualize a sequence of CPT codes based, at least in part, on the time of occurrence and/or semantics information, and predict the occurrence of one or more CPT codes in a care path. In one example embodiment, NLP module 207 implements a plurality of language modeling techniques to generate semantics information from CPT codes, e.g., neural-network-based models predict whether medical procedures occur together within a pre-defined time window of each other.

In one embodiment, the machine learning module 209 receives training data, e.g., training data 1012 illustrated in the training flow chart 1000, for training a machine learning model configured to determine a personalized care path for a patient based on the relevant data associated with the patient (e.g., the graph convolutional neural network-based model). In one example embodiment, the machine learning module 209 performs model training using training data, e.g., data from other modules, that contains input and correct output, to allow the model to learn over time. The training is performed based on the deviation of a processed result from a documented result when the inputs are fed into the machine learning model, e.g., an algorithm measures its accuracy through the loss function, adjusting until the error has been sufficiently minimized. In one embodiment, machine learning module 209 randomizes the ordering of the training data, visualizes the training data to identify relevant relationships between different variables, identifies any data imbalances, and splits the training data into two parts where one part is for training a model and the other part is for validating the trained model, de-duplicating, normalizing, correcting errors in the training data, and so on. Machine learning module 209 implements various machine learning techniques, e.g., k-nearest neighbors, cox proportional hazards model, decision tree learning, association rule learning, neural network (e.g., recurrent neural networks, graph convolutional neural networks, deep neural networks), inductive programming logic, support vector machines, Bayesian models, etc.

In one embodiment, the machine learning module 209 compares the generated care paths with an existing rule-based legacy care path generator to measure precision, recall, and scores for each of the generated care paths. In one example embodiment, the machine learning module 209 splits 80% of the CPT codes of each bucket as training and the remaining 20% as test data to measure the quality of bucket recommendation. In one embodiment, the machine learning module 209 tunes hyperparameter on validation data that is 20% of the randomly masked data from training. In one example embodiment, the machine learning module 209 measures parameters such as normalized discounted cumulative gain (NDCG), hit ratio, and/or recall. Furthermore, to assess the quality of learned representation, the machine learning module 209 performs qualitative analysis of CPT codes, buckets, and patients while projecting their representation in vector space model and assessing their semantic relatedness by visualizing their high dimensional embeddings by t-distributed stochastic neighborhood embedding (t-SNE) and principal component analysis (PCA). This analysis further assists in examining and understating the embedding layers. In one embodiment, the machine learning model trained by the machine learning module 209 is configured for care path pattern recognition to determine a pattern of care paths and to use the determined pattern for predictive analytics.

In one embodiment, the user interface module 211 enables a presentation of a graphical user interface (GUI) in the UE 103 that facilitates care path visualization. The user interface module 211 employs various application programming interfaces (APIs) or other function calls corresponding to the application 105 on the UE 103, thus enabling the display of graphics primitives such as icons, bar graphs, menus, buttons, data entry fields, etc. In another embodiment, the user interface module 211 causes interfacing of guidance information with the user 101 to include, at least in part, one or more annotations, audio messages, video messages, or a combination thereof pertaining to the generated care path. In one example embodiment, the user interface module 211 operates in connection with augmented reality (AR) processing techniques, wherein various applications, graphic elements, and features interact. In one example embodiment, the user 101 interacts with the GUI on the UE 103 to input data necessary for generating care paths or portions thereof and the user interface module 211 enables various displays of the resulting care paths. In such a manner, the user interface module 211 processes the received data and displays the results in a format that is understandable by the patients.

The above presented modules and components of the care path generating platform 111 are implemented in hardware, firmware, software, or a combination thereof. Though depicted as a separate entity in FIG. 2, it is contemplated that the care path generating platform 111 is also implemented for direct operation by the respective UE 103. As such, the care path generating platform 111 generates direct signal inputs by way of the operating system of the UE 103. In another embodiment, one or more of the modules 201-211 are implemented for operation by the respective UEs, as the care path generating platform 111. The various executions presented herein contemplate any and all arrangements and models.

Figure 3:
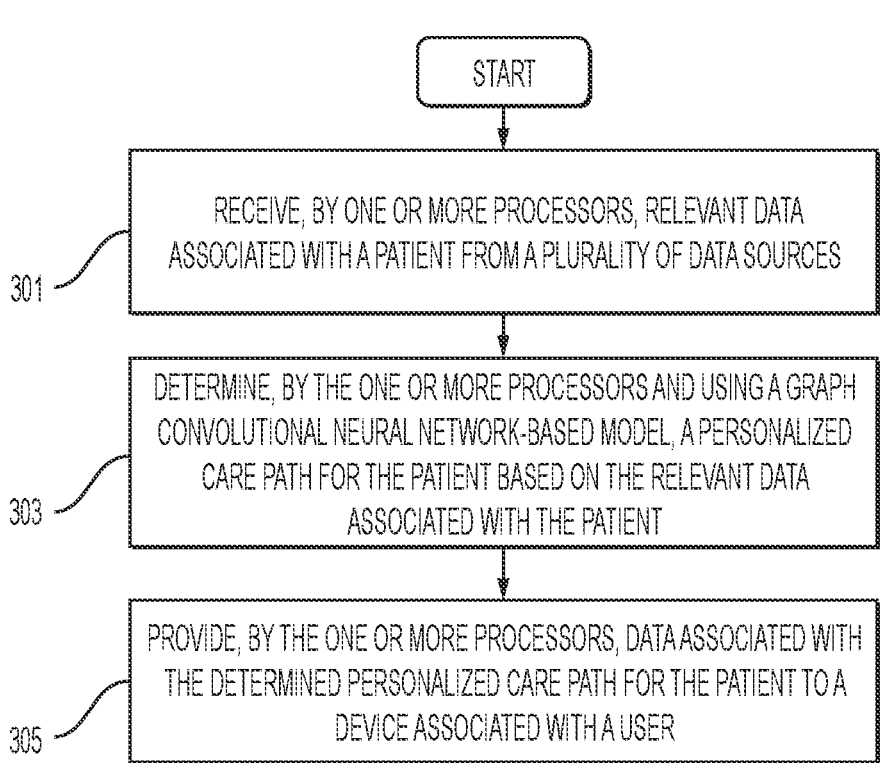
FIG. 3 is a flowchart of a process for generating personalized care paths for patients, according to some embodiments of the disclosure.
Figure 11:
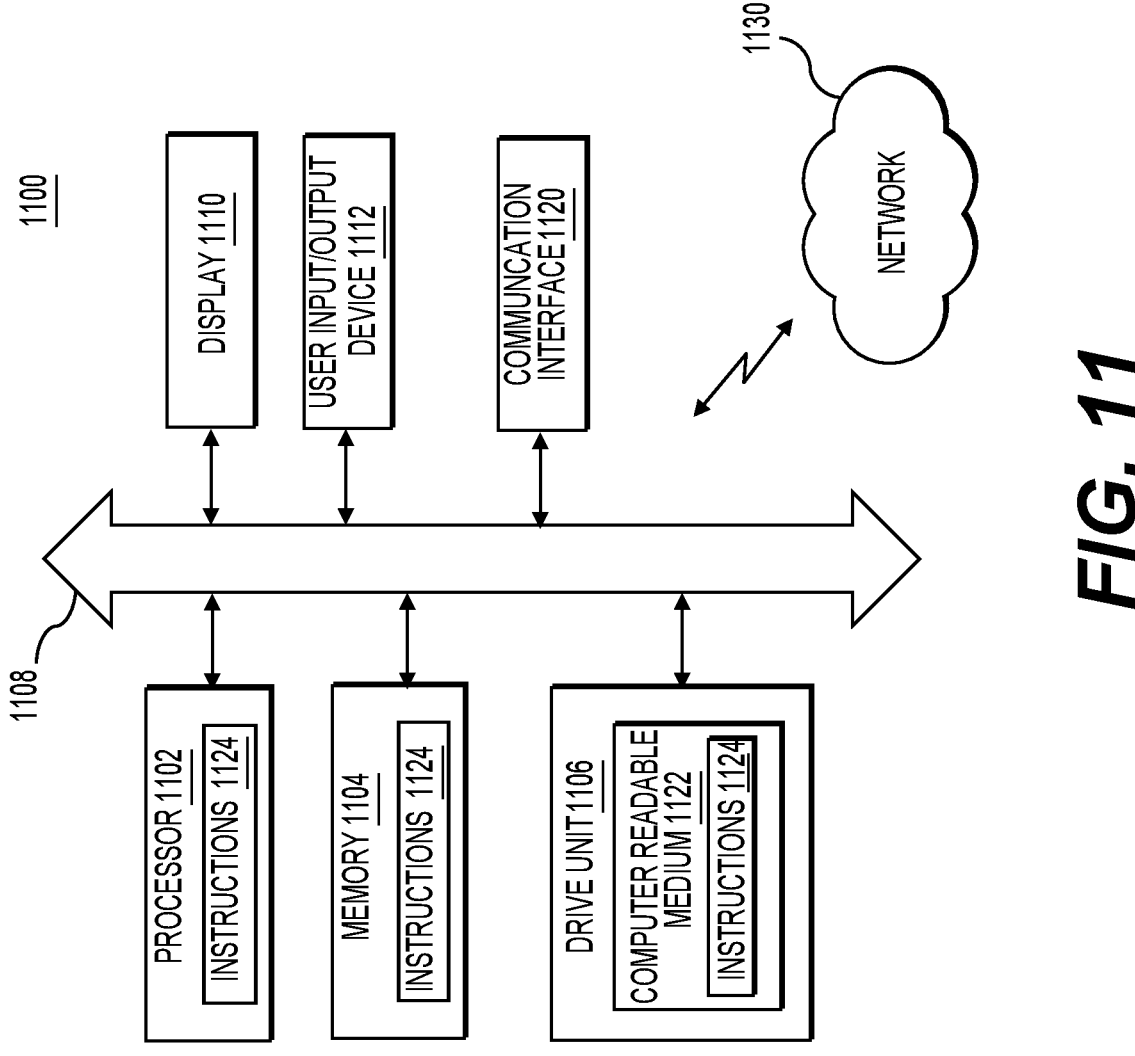
FIG. 11 illustrates an implementation of a computer system that executes techniques presented herein, according to some embodiments of the disclosure.

FIG. 3 is a flowchart of a process 300 for generating a personalized care path for a patient, according to some aspects of the disclosure. In various embodiments, the care path generating platform 111 and/or any of the modules 201-211 performs one or more portions of the process 300 and are implemented using, for instance, a chip set including a processor and a memory as shown in FIG. 11. As such, the care path generating platform 111 and/or any of modules 201-211 provide means for accomplishing various parts of the process 300, as well as means for accomplishing embodiments of other processes described herein in conjunction with other components of the system 100. Although the process 300 is illustrated and described as a sequence of steps, it is contemplated that various embodiments of the process 300 are performed in any order or combination and need not include all of the illustrated steps.

In step 301, the care path generating platform 111 receives, by one or more processors, relevant data associated with the patient from a plurality of data sources. In one embodiment, the relevant data includes demographic data and medical data associated with the patient. In one example embodiment, the demographic data includes age information, gender information, location information, income level, education level, household data, ethnic origin, employment data, marital status, children data, and/or languages spoken. In one example embodiment, the medical data includes patient's health condition, claim information, medication information, hospitalization information, lab information, and/or procedures information. In another embodiment, the relevant data includes patient characteristics data, claim characteristics data, provider characteristics data, and/or treatment characteristics data. In one embodiment, the plurality of data sources includes any potential information source that provides data associated with the patients.

In step 303, the care path generating platform 111 determines, by the one or more processors and using a graph convolutional neural network-based model, a personalized care path for a patient based on relevant data associated with the patient. In one embodiment, the graph convolutional neural network-based model is trained based on a plurality of care paths of a plurality of patients represented by a PBP graph. In one embodiment, each of the plurality of care paths includes a set of procedures and/or activities performed with respect to a corresponding one of the plurality of patients. The set of procedures and/or activities may be a part of a treatment plan. In one embodiment, each of the plurality of patients represented by the PBP graph is associated with a patient identifier and the relevant data associated with the patient. In one example embodiment, PBP interaction is a bipartite graph, and a graph convolutional neural network-based model is employed to learn graph embeddings and use them as a graph encoder to predict links between patients and procedures.

In one embodiment, the graph convolutional neural network-based model includes a patient aggregator configured to learn relatedness between the plurality of patients, a bucket aggregator configured to learn relatedness between the plurality of buckets, and a CPT aggregator configured to learn relatedness between the plurality of CPT codes. In one example embodiment, the patient aggregator generates a personalized patient embeddings by aggregating information of the one or more buckets and the CPT codes. In one example embodiment, the bucket aggregator summarizes the multi-item CPT code correlations in one or more corresponding buckets and combines the summarized CPT code correlations with the associated patients. In one example embodiment, the CPT codes aggregator collects the intent of the corresponding buckets to yield CPT codes embeddings.

In one embodiment, the PBP graph includes a plurality of patients, a plurality of buckets, and a plurality of CPT codes interconnected with each other. In the PBP graph, each of the plurality of buckets is linked to a corresponding patient. In the PBP graph, each of the plurality of CPT codes is linked to one or more corresponding buckets based, at least in part, on determining that the CPT code is included in the one or more corresponding buckets. In one embodiment, each bucket includes a plurality of CPT codes that are semantically related. In one embodiment, each bucket is determined based, at least in part, on one or more procedures or activities performed with respect to the corresponding patient during a pre-determined time period. The one or more procedures are represented by one or more CPT codes that correspond to the one or more procedures, respectively. In one embodiment, the CPT codes may be ordered chronologically, e.g., based on the time of the procedure or activity.

In step 305, the care path generating platform 111 provides, by the one or more processors, data associated with the determined personalized care path for the patient to a device associated with a user. In one example embodiment, the care path generating platform 111, via the user interface module 211, generates a display of the personalized care path or portions thereof. The personalized care path is presented in an easy-to-read and understand format, such as a graphical format or chart display showing the length of time for the total course of treatments, the type of treatments, the associated costs, and/or any other relevant information.

In one embodiment, the care path generating platform 111 causes a display of at least a portion of the data associated with the determined personalized care path for the patient via a graphical user interface (GUI) on the device. In one embodiment, at least a portion of the data associated with the determined personalized care path for the patient includes a set of procedures and/or activities constituting the determined personalized care path, a transaction variable associated with the determined personalized care path, a medical variable associated with the determined personalized care path, or a combination thereof. In one embodiment, the transaction variable is a cost estimate associated with the determined personalized care path, or each procedure/activity included therein. In one embodiment, the medical variable is a duration or an intensity associated with the determined personalized care path, or each procedure/activity included therein.

Figure 4:
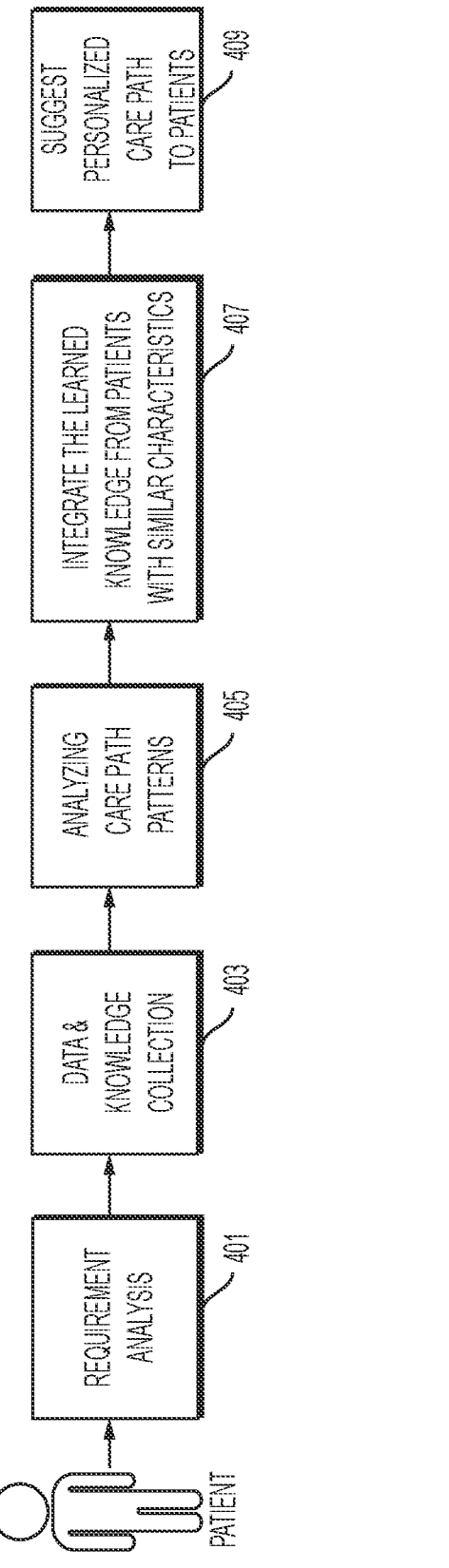
FIG. 4 is a flow diagram showing an example architecture for aggregating embeddings of nodes from a plurality of patients and generating personalized care paths, according to some embodiments of the disclosure.

FIG. 4 is a flow diagram that illustrates an example architecture for aggregating embeddings of nodes from a plurality of patients and utilizing the learned representation to suggest a personalized care path, according to some aspects of the disclosure. FIG. 4 further illustrates one or more steps of the process 300 to generate a personalized care path.

In step 401, the care path generating platform 111 performs requirement and character analysis of the patients for modeling care paths. In one embodiment, the care path generating platform 111 analyzes the requirements of corresponding applications for suggesting a personalized care path to the patients, and determines the characteristics of a patient's data based on the requirements. In one example embodiment, the characteristics of a patient's data that are needed to generate a personalized care path include demographic information, e.g., age, gender, or address, patient's condition information, claim information, medication information, hospitalization information, lab information, procedures information, and so on.

In step 403, the care path generating platform 111 collects and integrates relevant data associated with patients into the care path generation process based on the characteristics determined from the prior step 401.

In step 405, the care path generating platform 111 analyzes one or more care path patterns via advanced deep graph neural network techniques (e.g., the graph convolutional neural network-based model discussed elsewhere herein) and healthcare graph data generated based on the relevant data associated with the patients (e.g., the PBP graph). In one embodiment, the care path generating platform 111 generates a PBP graph architecture for modeling the care paths.

In step 407, the care path generating platform 111 integrates the learned knowledge from patients with similar characteristics, based on the care path patterns analyzed and learned from the prior step 405, to generate more accurately-tailored care paths for patients. In one embodiment, for a particular patient, the care path generating platform 111 analyzes various health datasets, by using a trained machine learning model that implements various analytics techniques, e.g., K-nearest neighbors algorithm, to identify patients with similar health profiles and then analyze their care path patterns in order to provide a personalized care path to the patient.

In step 409, the care path generating platform 111 suggests the personalized care path to a corresponding patient. Additionally, the care path quantitatively and qualitatively validates the correctness of the suggested care path by comparing the suggested care path to an existing rule-based legacy system as a baseline. For example, the care path generating platform 111 analyzes the performance of the suggested framework while measuring its performance.

Figure 5:
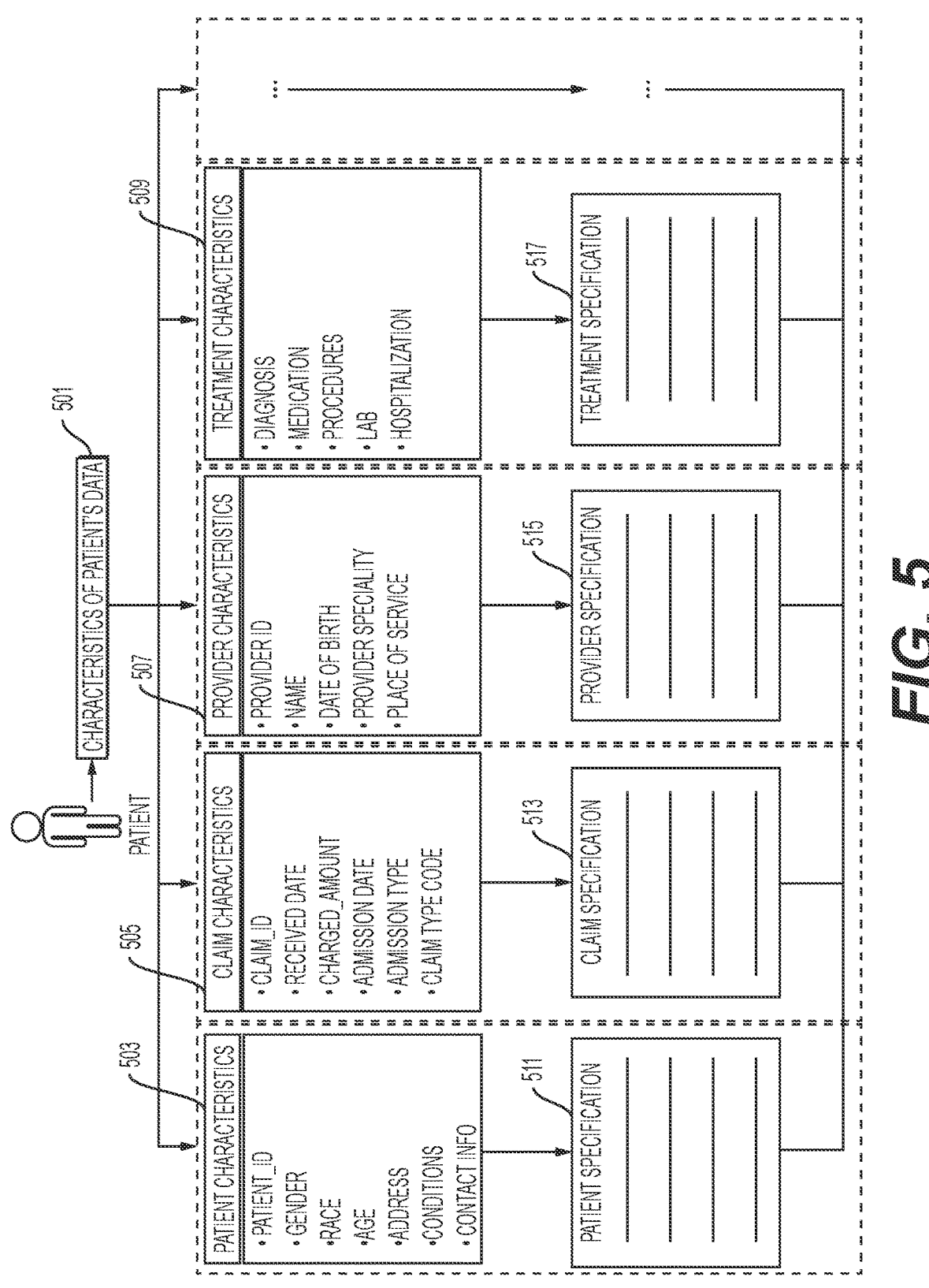
FIG. 5 is a diagram that illustrates the various characteristics associated with a patient that are used to generate a patient profile, according to some embodiments of the disclosure.

FIG. 5 illustrates the various characteristics associated with a patient that are used to generate a patient profile, according to aspects of the disclosure. In one embodiment, a patient profile includes information pertaining to the various types of characteristics illustrated in FIG. 5. The patient profile may be used in creating the PBP graph, finding other patients with similar characteristics, and training or using a machine learning model discussed in the present disclosure. A patient's characteristics explain various attributes of a patient, e.g., age, gender, address, and other demographic information. Each patient has a unique identification (ID) that is employed as a primary key to distinguish from other patients, and is used to identify patient profiles.

In one embodiment, the care path generating platform 111 classifies characteristics of patients data 501 into various categories, including patient characteristics 503, claim characteristics 505, provider characteristics 507, and treatment characteristics 509. In one example embodiment, the patient characteristics 503 include patient identification (ID), gender, race, age, address, health condition, and/or contact information. In one example embodiment, the claim characteristics 505 include claim identification (ID), received date, charged amount, admission date, admission type, and/or claim type codes. In one example embodiment, the provider characteristics 507 include provider identification (ID), name information, date of birth, provider specialty, and/or place of service. In one example embodiment, the treatment characteristics 509 include diagnosis, medication, procedures, lab results, and/or hospitalization information.

In one embodiment, the care path generating platform 111 collects and/or provides additional details on the various data within the patient characteristics 503, claim characteristics 505, provider characteristics 507, and treatment characteristics 509. In other words, the care path generating platform 111 may generate various "specifications" (e.g., a patient specification 511, a claim specification 513, a provider specification 515, and a treatment specification 517) that each include information pertaining to the corresponding set of characteristics (e.g., the patient characteristics 503, the claim characteristics 505, the provider characteristics 507, and the treatment characteristics 509, respectively). In one example embodiment, the patient specification 511 elaborates on information within the patient characteristics 503, e.g., a comprehensive description of the health condition of the patient. In one example embodiment, the claim specification 513 provides additional details on the data within the claim characteristics 505, e.g., a thorough explanation of the total amount charged for the medical procedures. In one example embodiment, the provider specification 515 goes into detail on the data within the provider characteristics 507, e.g., a comprehensive description of the provider's specialty. In one example embodiment, the treatment specification 517 explains the information within the treatment characteristics 509, e.g., a thorough description of the diagnosis of the patient.

Figure 6:
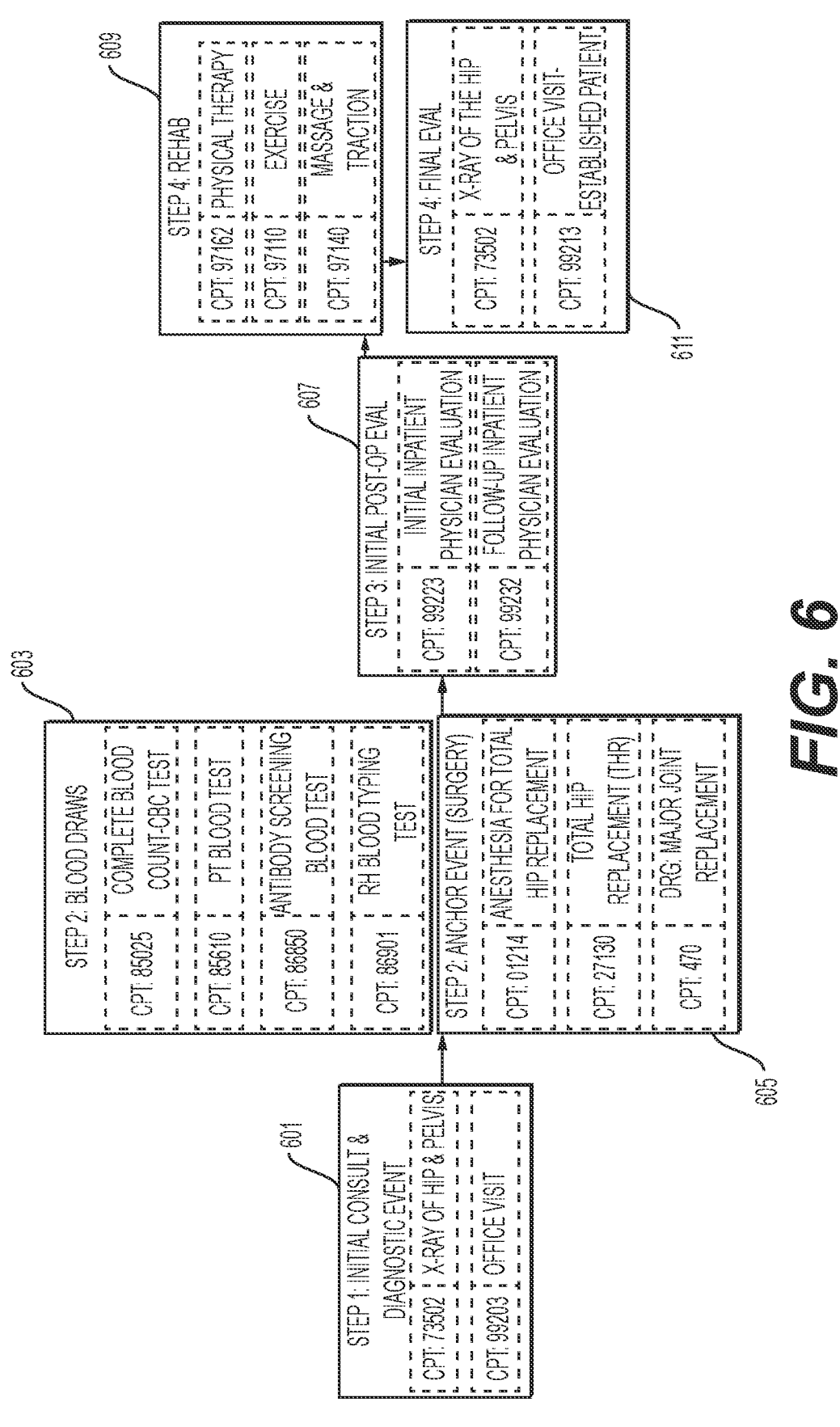
FIG. 6 is a flow diagram that illustrates a care path for a patient undergoing a surgical procedure, according to some embodiments of the disclosure.

FIG. 6 is a flow diagram that represents a care path for a patient undergoing a surgical procedure, according to one example embodiment. In one embodiment, the care path generating platform 111 categorizes the care path into a plurality of steps based, at least in part, on treatment characteristics and pre-defined time of occurrence of the treatment characteristics in the care path. In one example embodiment, the care path generating platform 111 categorizes the care path of a patient undergoing lumbar fusion into various steps: (i) initial consultation and diagnostic event, (ii) blood draws, (iii) anchor event (surgery), (iv) initial post-operation evaluation, (v) rehabilitation, and (vi) final evaluation.

In this example embodiment, in step 601, the surgical procedure for lumbar fusion commences with an initial consultation with a physician, e.g., office visits, that is followed by a diagnostic event, e.g., consultation regarding the X-ray of the hip and pelvis. In step 603, a blood test is performed on the patient, which includes several steps, e.g., complete blood count (CBC) test, PT blood test, antibody screening blood test, and/or RH blood typing test. In step 605, the surgical procedure is performed on the patient, which includes administering anesthesia for total Hip replacement, total hip replacement (THR), and DRG: major joint replacement. In step 607, an initial post-operation evaluation is conducted by a physician, and a follow-up inpatient physician evaluation is scheduled. In step 609, the patient undergoes post-operation rehabilitation such as physical therapy, exercises, and/or massages and tractions. In step 611, a final evaluation is performed that includes an X-ray of the operated hip and pelvis, and a follow-up visit with the physician. It is to be noted that one or more procedures and/or activities performed within the categorized care path are represented by the respective CPT codes.

Figure 7:
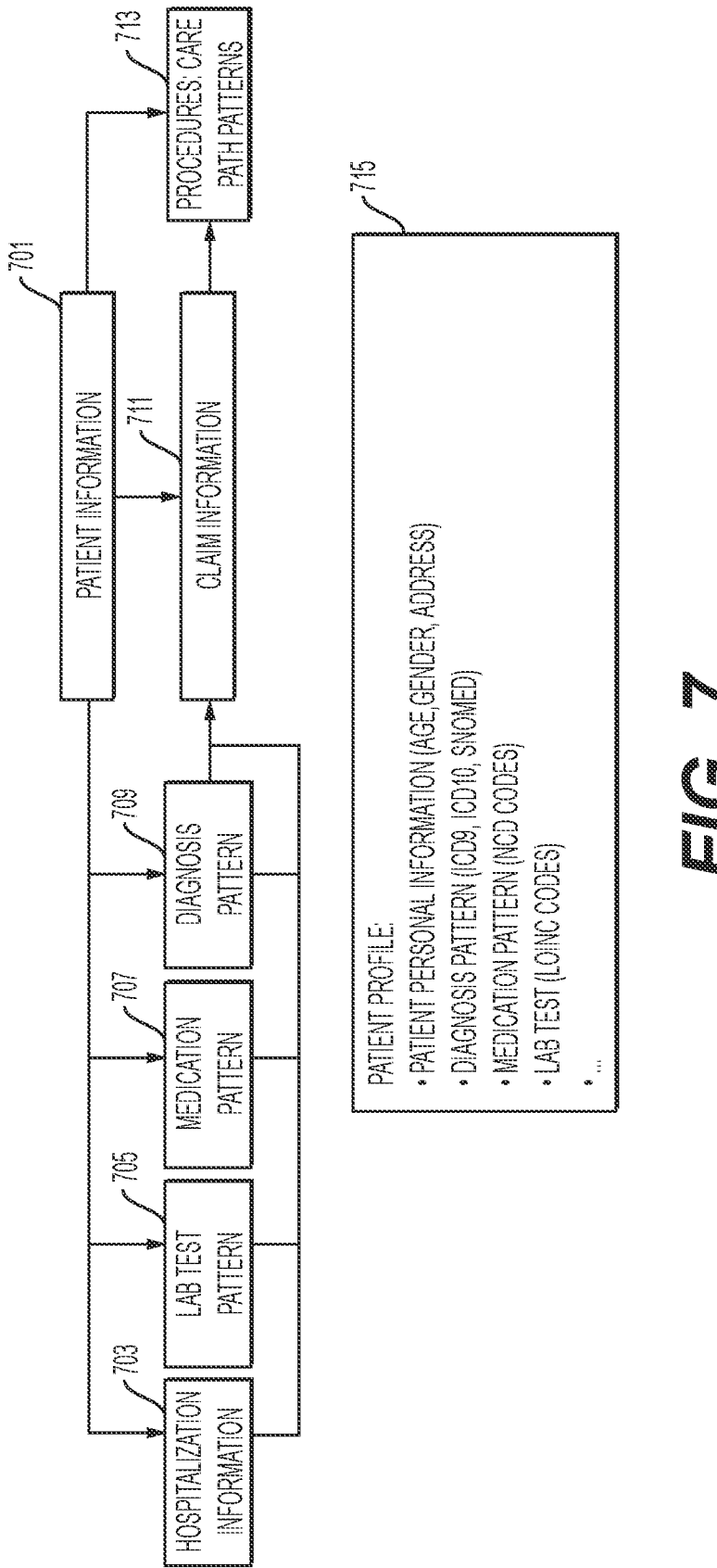
FIG. 7 is a diagram showing an example of a process for integrating patient data with other relevant data sources to generate a patient profile, according to some embodiments of the disclosure.

FIG. 7 is a diagram that illustrates an integration of patient data with other relevant data sources to generate a patient profile, according to some aspects of the disclosure. In one embodiment, the care path generating platform 111 integrates heterogeneous patient information 701 including, e.g., hospitalization information 703, laboratory test pattern(s) 705, medication pattern(s) 707, diagnosis pattern(s) 709, and claim information 711, to represent care path pattern(s) 713.

In one embodiment, the care path generating platform 111 employs health care graphs that associate each patient with a set of diagnosis codes (e.g., international classification of diseases, ninth revision (ICD9), international classification of diseases, tenth revision (ICD 10), systematized nomenclature of medicine clinical terms (SNOMED) codes), medication codes (e.g., national drug code (NDC)), and lab tests (e.g., logical observation identifier names and codes (LOINC) codes). Furthermore, the care path generating platform 111 extracts medical code descriptions, e.g., ICD9 and NDC codes, from publicly available data sources, and incorporates the extracted codes to generate a patient profile 715. The patient profile 715 also contains demographic information including age, gender, and address. The generated patient profile 715 is inputted to the graph convolutional neural network-based model employing, e.g., the PBP graph. In one embodiment, the care path generating platform 111 contextualizes the sequence of CPT codes by their time of occurrence. To further add semantics to the CPT codes, the care path generating platform 111 buckets the sequence of CPT codes based on the time windows that they occurred, e.g., 60 days, 45 days, etc. There may be an implicit relation between CPT codes that occurred on consecutive days. In another embodiment, the care path generating platform 111 utilizes an NLP-based approach to contextualize the sequence of CPT codes by their descriptions. In one example embodiment, the care path generating platform 111 integrates clinical data from various databases, e.g., PubMed, MIMIC-III, etc., with the CPT codes description. The care path generating platform 111 then computes lower dimensional word representation to further enhance the quality of buckets in terms of relatedness and semantics. The care path generating platform 111 utilizes the fine-grained buckets of CPT codes for building the PBP graph.

Figure 8:
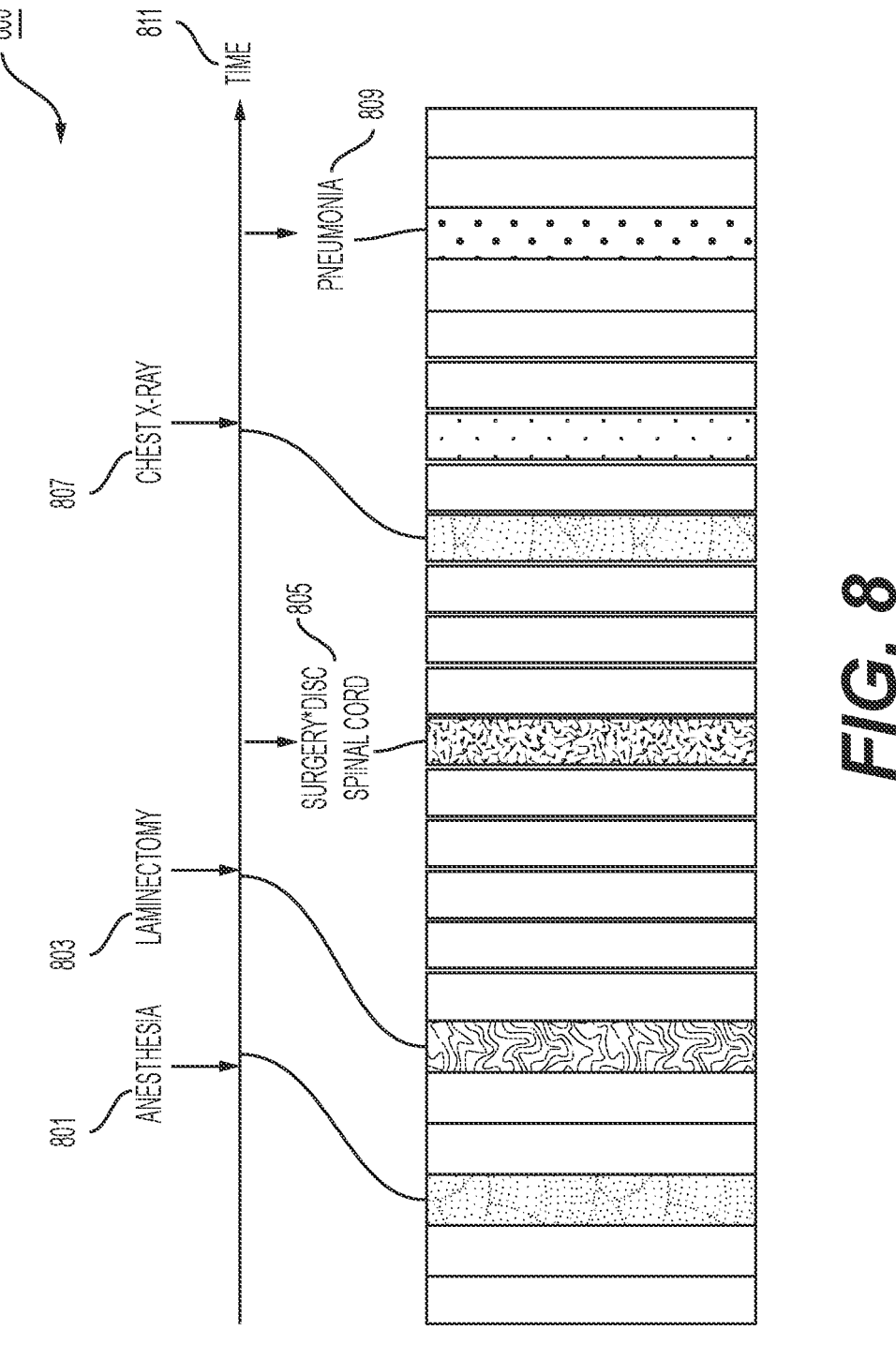
FIG. 8 is a diagram that illustrates a process of bucketing a sequence of current procedural terminology (CPT) codes based on their time of occurrence during a specific medical procedure, according to some embodiments of the disclosure.

FIG. 8 illustrates bucketing a sequence of CPT codes based on the time of occurrence of the corresponding procedures/activities, according to some aspect of the disclosure. In other words, FIG. 8 illustrates an example bucket 800 that organizes a plurality of CPT codes that occurred within a pre-determined time frame chronologically. In one example embodiment, the care path generating platform 111 monitors, in real-time or near real-time, the occurrence of CPT codes in similar medical procedures, and collects the CPT codes in the bucket 800. In another embodiment, the care path generating platform 111 monitors medical procedures for patients with similar characteristics and collects the CPT codes in the bucket 800. The care path generating platform 111 determines the relation between the CPT procedures based on their time of occurrence and orders them chronologically. As an example, the care path generating platform 111 monitors CPT codes and the chronology of their occurrence during a surgical procedure, e.g., lumbar fusion. The care path generating platform 111 collects the CPT codes for the corresponding procedures/activities, e.g., an anesthesia 801, a laminectomy 803, a disc and spinal cord surgery 805, a chest X-ray 807, and/or a Pneumonia 809, during time frame 811 for the surgical procedure, e.g., lumbar fusion. The care path generating platform 111 then organizes the CPT codes chronologically in the bucket 800 for use in the PBP graph and care path generation.

Figure 9:
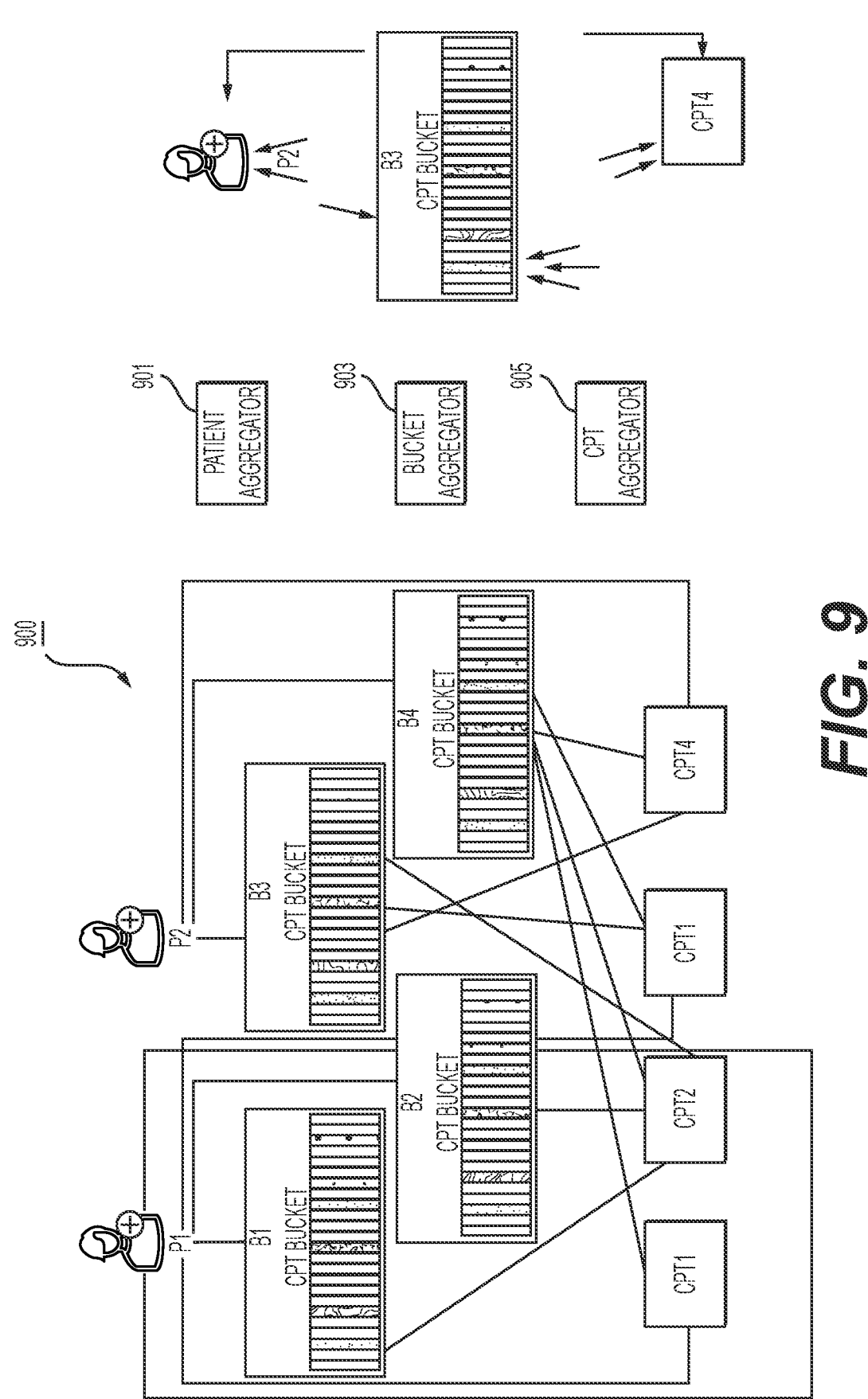
FIG. 9 is a diagram that illustrates a PBP graph structure, according to some embodiments of the disclosure.

FIG. 9 illustrates an example PBP graph structure, according to some aspects of the disclosure. A PBP graph 900 represents the interaction between patients (e.g., P={P1, P2 ... $P_{|P|}$}), buckets (e.g., B={B1, B2, B3, B4 ... $B_{|P|}$}), and medical procedures represented by the corresponding CPT codes (e.g., procedures={$CPT_1$, $CPT_2$, $CPT_3$, $CPT_4$ ... $CPT_{|P|}$}. In one embodiment, the PBP graph 900 is used to predict the link between bucket nodes and CPT codes, e.g., each bucket contains a set of CPT codes that occurred within a time frame, e.g., pre-defined consecutive days, for a plurality of patients. The bucket nodes are incorporated to represent the semantics of patients' care paths. In this example embodiment, the PBP graph 900 associates the patient P1 with the bucket B1 and the bucket B2 each comprising the $CPT_2$ code, and the patient P2 is associated with the bucket B3 comprising the $CPT_2$ and $CPT_4$ codes and the bucket B4 comprising the $CPT_1$, the $CPT_2$, the $CPT_3$, and the $CPT_4$ codes. The PBP graph 900 is then used to predict CPT codes for the bucket B3 for the patient P2 based on the semantics of the CPT codes within the buckets and the preference information of the patients. Particularly, in one embodiment, a graph convolutional neural network-based model is used to learn the interactions between the patients, buckets, and CPT codes represented in the PBP graph, and make a prediction as to which care path represented by a bucket is most appropriate for the subject patient.

In one embodiment, the recursive learning procedures and multi-layer structure of the proposed framework captures high-order information over the PBP graph 900. More specifically, three different aggregators are developed for the patients, the buckets, and the procedures. These three aggregators are built upon the heterogeneous interactive layers to retrieve both heterogeneous nodes and linkage signals in the PBP graph 900. In one embodiment, a patient aggregator 901 generates personalized patient embeddings by aggregating the information of all buckets and CPT codes, a bucket aggregator 903 summarizes the multi-CPT code correlations inside corresponding buckets and combines them with the associated patient, and a CPT codes aggregator 905 yields CPT code embeddings by collecting the intent of their corresponding buckets. In such a manner, the bucket B3 is modeled based on patient-procedure collaborative filtering signals and procedure-to-procedure relationships.

In one embodiment, using a graph convolutional neural network-based model, the PBP graph 900 models care path generation tasks as predicting the interactions, e.g., heterogeneous interactions among the patients, buckets, and medical procedures over the PBP graph 900, while designing heterogeneous aggregators (e.g., 901, 903, and 905) that learn the embeddings of each node. In one embodiment, the output layer of the graph convolutional neural network-based model ranks the results from the learned embeddings, and the interactive layers of the PBP graph 900 models patient-procedure, bucket-procedure, and patient-bucket interactive signals.

Figure 10:
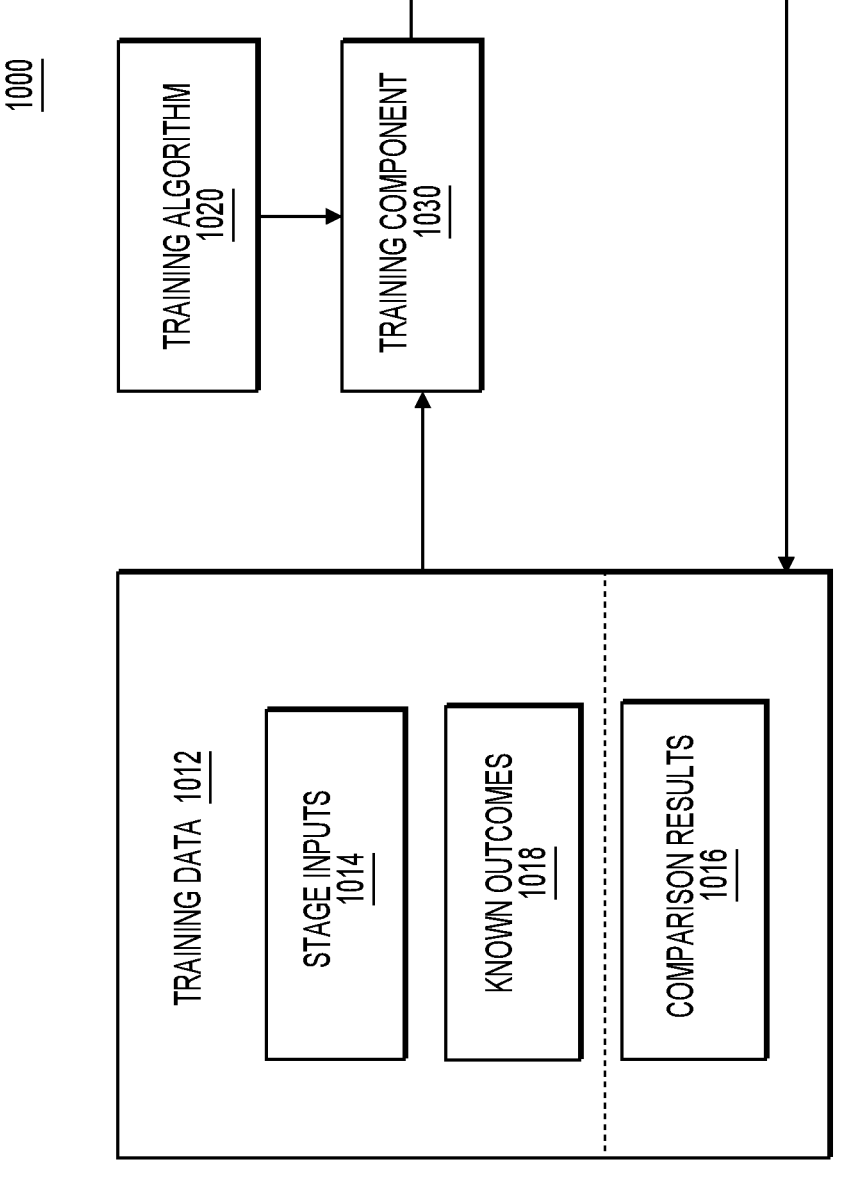
FIG. 10 shows an example machine learning training flow chart, according to some embodiments of the disclosure.

One or more implementations disclosed herein include and/or are implemented using a machine learning model, e.g., machine learning module 209. For example, one or more of the modules of the care path generating platform 111 are implemented using a machine learning model and/or are used to train the machine learning model, e.g., machine learning module 209. A given machine learning model is trained using the training flow chart 1000 of FIG. 10. Training data 1012 includes one or more of stage inputs 1014 and known outcomes 1018 related to the machine learning model to be trained. Stage inputs 1014 are from any applicable source including text, visual representations, data, values, comparisons, and stage outputs, e.g., one or more outputs from one or more steps from FIG. 3. The known outcomes 1018 are included for the machine learning models generated based on supervised or semi-supervised training. An unsupervised machine learning model may not be trained using known outcomes 1018. Known outcomes 1018 includes known or desired outputs for future inputs similar to or in the same category as stage inputs 1014 that do not have corresponding known outputs.

The training data 1012 and a training algorithm 1020, e.g., one or more of the modules implemented using the machine learning model and/or are used to train the machine learning model, is provided to a training component 1030 that applies the training data 1012 to the training algorithm 1020 to generate the machine learning model. According to an implementation, the training component 1030 is provided comparison results 1016 that compare a previous output of the corresponding machine learning model to apply the previous result to re-train the machine learning model. The comparison results 1016 are used by training component 1030 to update the corresponding machine learning model. The training algorithm 1020 utilizes machine learning networks and/or models including, but not limited to a deep learning network such as Deep Neural Networks (DNN), Convolutional Neural Networks (CNN), Fully Convolutional Networks (FCN) and Recurrent Neural Networks (RCN), probabilistic models such as Bayesian Networks and Graphical Models, classifiers such as K-Nearest Neighbors, and/or discriminative models such as Decision Forests and maximum margin methods, the model specifically discussed herein, or the like.

The machine learning model used herein is trained and/or used by adjusting one or more weights and/or one or more layers of the machine learning model. For example, during training, a given weight is adjusted (e.g., increased, decreased, removed) based on training data or input data. Similarly, a layer is updated, added, or removed based on training data/and or input data. The resulting outputs are adjusted based on the adjusted weights and/or layers.

In general, any process or operation discussed in this disclosure is understood to be computer-implementable, such as the process illustrated in FIG. 3 are performed by one or more processors of a computer system as described herein. A process or process step performed by one or more processors is also referred to as an operation. The one or more processors are configured to perform such processes by having access to instructions (e.g., software or computer-readable code) that, when executed by one or more processors, cause one or more processors to perform the processes. The instructions are stored in a memory of the computer system. A processor is a central processing unit (CPU), a graphics processing unit (GPU), or any suitable type of processing unit.

A computer system, such as a system or device implementing a process or operation in the examples above, includes one or more computing devices. One or more processors of a computer system are included in a single computing device or distributed among a plurality of computing devices. One or more processors of a computer system are connected to a data storage device. A memory of the computer system includes the respective memory of each computing device of the plurality of computing devices.

FIG. 11 illustrates an implementation of a computer system that executes techniques presented herein. The computer system 1100 includes a set of instructions that are executed to cause the computer system 1100 to perform any one or more of the methods or computer based functions disclosed herein. The computer system 1100 operates as a standalone device or is connected, e.g., using a network, to other computer systems or peripheral devices.

Unless specifically stated otherwise, as apparent from the following discussions, it is appreciated that throughout the specification, discussions utilizing terms such as "processing," "computing," "calculating," "determining", "analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" refers to any device or portion of a device that processes electronic data, e.g., from registers and/or memory to transform that electronic data into other electronic data that, e.g., is stored in registers and/or memory. A "computer," a "computing machine," a "computing platform," a "computing device," or a "server" includes one or more processors.

In a networked deployment, the computer system 1100 operates in the capacity of a server or as a client user computer in a server-client user network environment, or as a peer computer system in a peer-to-peer (or distributed) network environment. The computer system 1100 is also implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In a particular implementation, the computer system 1100 is implemented using electronic devices that provide voice, video, or data communication. Further, while the computer system 1100 is illustrated as a single system, the term "system" shall also be taken to include any collection of systems or sub-systems that individually or jointly execute a set, or multiple sets, of instructions to perform one or more computer functions.

As illustrated in FIG. 11, the computer system 1100 includes a processor 1102, e.g., a central processing unit (CPU), a graphics processing unit (GPU), or both. The processor 1102 is a component in a variety of systems. For example, the processor 1102 is part of a standard personal computer or a workstation. The processor 1102 is one or more processors, digital signal processors, application specific integrated circuits, field programmable gate arrays, servers, networks, digital circuits, analog circuits, combinations thereof, or other now known or later developed devices for analyzing and processing data. The processor 1102 implements a software program, such as code generated manually (i.e., programmed).

The computer system 1100 includes a memory 1104 that communicates via bus 1108. Memory 1104 is a main memory, a static memory, or a dynamic memory. Memory 1104 includes, but is not limited to computer-readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, the memory 1104 includes a cache or random-access memory for the processor 1102. In alternative implementations, the memory 1104 is separate from the processor 1102, such as a cache memory of a processor, the system memory, or other memory. Memory 1104 is an external storage device or database for storing data. Examples include a hard drive, compact disc ("CD"), digital video disc ("DVD"), memory card, memory stick, floppy disc, universal serial bus ("USB") memory device, or any other device operative to store data. The memory 1104 is operable to store instructions executable by the processor

1102. The functions, acts, or tasks illustrated in the figures or described herein are performed by processor 1102 executing the instructions stored in memory 1104. The functions, acts, or tasks are independent of the particular type of instruction set, storage media, processor, or processing strategy and are performed by software, hardware, integrated circuits, firmware, micro-code, and the like, operating alone or in combination. Likewise, processing strategies include multiprocessing, multitasking, parallel processing, and the like.

As shown, the computer system 1100 further includes a display 1110, such as a liquid crystal display (LCD), an organic light emitting diode (OLED), a flat panel display, a solid-state display, a cathode ray tube (CRT), a projector, a printer or other now known or later developed display device for outputting determined information. The display 1110 acts as an interface for the user to see the functioning of the processor 1102, or specifically as an interface with the software stored in the memory 1104 or in the drive unit 1106.

Additionally or alternatively, the computer system 1100 includes an input/output device 1112 configured to allow a user to interact with any of the components of the computer system 1100. The input/output device 1112 is a number pad, a keyboard, a cursor control device, such as a mouse, a joystick, touch screen display, remote control, or any other device operative to interact with the computer system 1100.

The computer system 1100 also includes the drive unit 1106 implemented as a disk or optical drive. The drive unit 1106 includes a computer-readable medium 1122 in which one or more sets of instructions 1124, e.g. software, is embedded. Further, the sets of instructions 1124 embodies one or more of the methods or logic as described herein. Instructions 1124 resides completely or partially within memory 1104 and/or within processor 1102 during execution by the computer system 1100. The memory 1104 and the processor 1102 also include computer-readable media as discussed above.

In some systems, computer-readable medium 1122 includes the set of instructions 1124 or receives and executes the set of instructions 1124 responsive to a propagated signal so that a device connected to network 1130 communicates voice, video, audio, images, or any other data over network 1130. Further, the sets of instructions 1124 are transmitted or received over the network 1130 via the communication port or interface 1120, and/or using the bus 1108. The communication port or interface 1120 is a part of the processor 1102 or is a separate component. The communication port or interface 1120 is created in software or is a physical connection in hardware. The communication port or interface 1120 is configured to connect with the network 1130, external media, display 1110, or any other components in the computer system 1100, or combinations thereof. The connection with network 1130 is a physical connection, such as a wired Ethernet connection, or is established wirelessly as discussed below. Likewise, the additional connections with other components of the computer system 1100 are physical connections or are established wirelessly. Network 1130 alternatively be directly connected to the bus 1108.

While the computer-readable medium 1122 is shown to be a single medium, the term "computer-readable medium" includes a single medium or multiple media, such as a centralized or distributed database, and/or associated caches and servers that store one or more sets of instructions. The term "computer-readable medium" also includes any medium that is capable of storing, encoding, or carrying a set of instructions for execution by a processor or that causes a computer system to perform any one or more of the methods or operations disclosed herein. The computer-readable medium 1122 is non-transitory, and may be tangible.

The computer-readable medium 1122 includes a solid-state memory such as a memory card or other package that houses one or more non-volatile read-only memories. The computer-readable medium 1122 is a random-access memory or other volatile re-writable memory. Additionally or alternatively, the computer-readable medium 1122 includes a magneto-optical or optical medium, such as a disk or tapes or other storage device to capture carrier wave signals such as a signal communicated over a transmission medium. A digital file attachment to an e-mail or other self-contained information archive or set of archives is considered a distribution medium that is a tangible storage medium. Accordingly, the disclosure is considered to include any one or more of a computer-readable medium or a distribution medium and other equivalents and successor media, in which data or instructions are stored.

In an alternative implementation, dedicated hardware implementations, such as application specific integrated circuits, programmable logic arrays, and other hardware devices, is constructed to implement one or more of the methods described herein. Applications that include the apparatus and systems of various implementations broadly include a variety of electronic and computer systems. One or more implementations described herein implement functions using two or more specific interconnected hardware modules or devices with related control and data signals that are communicated between and through the modules, or as portions of an application-specific integrated circuit. Accordingly, the present system encompasses software, firmware, and hardware implementations.

Computer system 1100 is connected to network 1130. Network 1130 defines one or more networks including wired or wireless networks. The wireless network is a cellular telephone network, an 802.11, 802.16, 802.20, or WiMAX network. Further, such networks include a public network, such as the Internet, a private network, such as an intranet, or combinations thereof, and utilizes a variety of networking protocols now available or later developed including, but not limited to TCP/IP based networking protocols. Network 1130 includes wide area networks (WAN), such as the Internet, local area networks (LAN), campus area networks, metropolitan area networks, a direct connection such as through a Universal Serial Bus (USB) port, or any other networks that allows for data communication. Network 1130 is configured to couple one computing device to another computing device to enable communication of data between the devices. Network 1130 is generally enabled to employ any form of machine-readable media for communicating information from one device to another. Network 1130 includes communication methods by which information travels between computing devices. Network 1130 is divided into sub-networks. The sub-networks allow access to all of the other components connected thereto or the sub-networks restrict access between the components. Network 1130 is regarded as a public or private network connection and includes, for example, a virtual private network or an encryption or other security mechanism employed over the public Internet, or the like.

In accordance with various implementations of the present disclosure, the methods described herein are implemented by software programs executable by a computer system. Further, in an example, non-limited implementation, implementations can include distributed processing, component/object distributed processing, and parallel processing. Alternatively, virtual computer system processing can be constructed to implement one or more of the methods or functionality as described herein.

Although the present specification describes components and functions that are implemented in particular implementations with reference to particular standards and protocols, the disclosure is not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

It will be understood that the steps of methods discussed are performed in one embodiment by an appropriate processor (or processors) of a processing (i.e., computer) system executing instructions (computer-readable code) stored in storage. It will also be understood that the disclosure is not limited to any particular implementation or programming technique and that the disclosure is implemented using any appropriate techniques for implementing the functionality described herein. The disclosure is not limited to any particular programming language or operating system.

It should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention are practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications are made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted except in light of the attached claims and their equivalents.

The present disclosure furthermore relates to the following aspects.

Example 1. A computer-implemented method for generating a personalized care path for a patient, comprising: receiving, by one or more processors, relevant data associated with the patient from a plurality of data sources, wherein the relevant data includes demographic data and medical data associated with the patient; determining, by the one or more processors and using a graph convolutional neural network-based model, the personalized care path for the patient based on the relevant data associated with the patient, wherein the graph convolutional neural network-based model is trained based on a plurality of care paths of a plurality of patients represented by a patient-bucket-procedure (PBP) graph; and providing, by the one or more processors, data associated with the determined personalized care path for the patient to a device associated with a user.

Example 2. The computer-implemented method of example 1, wherein the PBP graph includes: the plurality of patients; a plurality of buckets, wherein each bucket is linked to a corresponding patient of the plurality of patients; and a plurality of current procedural terminology (CPT) codes, wherein each of the plurality of CPT codes is linked to one or more corresponding buckets of the plurality of buckets.

Example 3. The computer-implemented method of example 2, wherein each of the plurality of buckets is determined by: determining, by the one or more processors, one or more procedures performed with respect to the corresponding patient during a pre-determined time period; determining, by the one or more processors, one or more of the plurality of CPT codes corresponding to the one or more procedures; and ordering, by the one or more processors, the one or more CPT codes chronologically.

Example 4. The computer-implemented method of example 2 or 3, wherein each of the plurality of CPT codes is included in the one or more corresponding buckets.

Example 5. The computer-implemented method of example 2, 3, or 4, wherein each of the plurality of buckets includes a set of CPT codes that are semantically related.

Example 6. The computer-implemented method of example 2, 3, 4, or 5, wherein the graph convolutional neural network-based model includes: a patient aggregator configured to learn relatedness between the plurality of patients; a bucket aggregator configured to learn relatedness between the plurality of buckets; and a CPT aggregator configured to learn relatedness between the plurality of CPT codes.

Example 7. The computer-implemented method of any of the preceding examples, wherein each of the plurality of care paths includes at least one of procedures or activities performed with respect to a corresponding one of the plurality of patients.

Example 8. The computer-implemented method of example 7, wherein the at least one of procedures or activities is part of a treatment plan.

Example 9. The computer-implemented method of any of the preceding examples, wherein the demographic data includes at least one of: age information, gender information, location information, income level, education level, household data, ethnic origin, employment data, marital status, children data, or languages spoken.

Example 10. The computer-implemented method of any of the preceding examples, wherein the medical data includes at least one of: health condition, claim information, medication information, hospitalization information, lab information, or procedures information.

Example 11. The computer-implemented method of any of the preceding examples, further comprising: causing to be displayed, by the one or more processors, at least a portion of the data associated with the determined personalized care path for the patient via a graphical user interface (GUI) on the device.

Example 12. The computer-implemented method of example 11, wherein the at least the portion of the data associated with the determined personalized care path for the patient includes at least one of: at least one of procedures or activities constituting the determined personalized care path; a transaction variable associated with the determined personalized care path; or a medical variable associated with the determined personalized care path.

Example 13. The computer-implemented method of example 12, wherein the transaction variable is a cost estimate associated with the determined personalized care path.

Example 14. The computer-implemented method of example 12 or 13, wherein the medical variable is a duration or an intensity associated with the determined personalized care path.

Example 15. A system comprising: one or more processors; and at least one non-transitory computer readable medium storing instructions which, when executed by the one or more processors, cause the one or more processors to perform operations comprising: receiving relevant data associated with the patient from a plurality of data sources, wherein the relevant data includes demographic data and medical data associated with the patient; determining, using a graph convolutional neural network-based model, the personalized care path for the patient based on the relevant data associated with the patient, wherein the graph convolutional neural network-based model is trained based on a plurality of care paths of a plurality of patients represented by a patient-bucket-procedure (PBP) graph; and providing data associated with the determined personalized care path for the patient to a device associated with a user.

Example 16. The system of example 15, wherein the PBP graph includes: the plurality of patients; a plurality of buckets, wherein each bucket is linked to a corresponding patient of the plurality of patients; and a plurality of current procedural terminology (CPT) codes, wherein each of the plurality of CPT codes is linked to one or more corresponding buckets of the plurality of buckets.

Example 17. The system of example 16, wherein each of the plurality of buckets is determined by: determining one or more procedures performed with respect to the corresponding patient during a pre-determined time period; determining one or more of the plurality of CPT codes corresponding to the one or more procedures; and ordering the one or more CPT codes chronologically.

Example 18. The system of example 16 or 17, wherein each of the plurality of CPT codes is included in the one or more corresponding buckets.

Example 19. A non-transitory computer readable medium storing instructions which, when executed by one or more processors, cause the one or more processors to perform operations comprising: receiving relevant data associated with the patient from a plurality of data sources, wherein the relevant data includes demographic data and medical data associated with the patient; determining, using a graph convolutional neural network-based model, the personalized care path for the patient based on the relevant data associated with the patient, wherein the graph convolutional neural network-based model is trained based on a plurality of care paths of a plurality of patients represented by a patient-bucket-procedure (PBP) graph; and providing data associated with the determined personalized care path for the patient to a device associated with a user.

Example 20. The non-transitory computer readable medium of example 19, wherein the PBP graph includes: the plurality of patients; a plurality of buckets, wherein each bucket is linked to a corresponding patient of the plurality of patients; and a plurality of current procedural terminology (CPT) codes, wherein each of the plurality of CPT codes is linked to one or more corresponding buckets of the plurality of buckets.

What is claimed is:

1. A computer-implemented method comprising:
   receiving, by one or more processors, a plurality of training datasets associated with a plurality of patients, the plurality of training datasets including (i) a plurality of relevant data associated with the plurality of patients including demographic data and medical data associated with the plurality of patients and (ii) a plurality of known care paths for the plurality of patients, wherein each known care path of the plurality of known care paths includes one or more known procedures, from a plurality of procedures, undergone by a respective patient;
   generating, by the one or more processors and based on the plurality of training datasets, a patient-bucket-procedure (PBP) graph, the PBP graph including:
   (i) a plurality of nodes comprising (a) a plurality of patient nodes representing the plurality of relevant data associated with the plurality of patients, (b) a plurality of procedure code nodes representing a plurality of procedure codes for the plurality of procedures, and (c) a plurality of bucket nodes for the plurality of patients that represent the plurality of known care paths for the plurality of patients, and
   (ii) a plurality of links comprising (a) first links between the plurality of bucket nodes and the plurality of patient nodes corresponding to the plurality of patients, and (b) second links between the plurality of bucket nodes and the plurality of procedure code nodes representing procedure codes for the one or more known procedures;

defining, by the one or more processors and based on a structure of the PBP graph, an architecture of a graph convolutional neural network-based model, the architecture including (i) an input layer configured to receive input data, (ii) a plurality of embedding layers configured for use with a plurality of heterogenous aggregators to learn an embedding of each node of the plurality of patient nodes, the plurality of bucket nodes, and the plurality of procedure code nodes by modeling interactive signals, and (iii) an output layer configured to generate output data based on the learned embeddings;
   training, by the one or more processors using the PBP graph and based on the plurality of training datasets, the graph convolutional neural network-based model;
   receiving, by the one or more processors and via the input layer of the trained graph convolutional neural network-based model, new relevant data associated with a new patient including demographic data and medical data associated with the new patient as the input data;
   identifying, by the one or more processors and via the plurality of embedding layers of the trained graph convolutional neural network-based model, (i) a patient from the plurality of patients similar to the new patient and (ii) one or more procedures represented by one of the plurality of bucket nodes corresponding to the patient;
   generating, by the one or more processors and via the output layer of the trained graph convolutional neural network-based model, a personalized care path for the new patient as the output data, the personalized care path including the one or more procedures identified; and
   providing, by the one or more processors, data associated with the personalized care path for the new patient to a device associated with a user.

2. The computer-implemented method of claim 1, wherein the plurality of procedure code nodes include a plurality of current procedural terminology (CPT) codes corresponding to the plurality of procedures, and wherein the plurality of bucket nodes are determined by:
   determining, by the one or more processors, the one or more known procedures included in the plurality of known care paths, the one or more known procedures occurring during a pre-determined time period;
   determining, by the one or more processors, one or more of the plurality of CPT codes corresponding to the one or more known procedures; and
   ordering, by the one or more processors, the one or more of the plurality of CPT codes chronologically within the plurality of bucket nodes based on an occurrence of the one or more known procedures during the pre-determined time period.

3. The computer-implemented method of claim 2, wherein each of the plurality of CPT codes is included in one or more of the plurality of bucket nodes.

4. The computer-implemented method of claim 2, wherein each of the plurality of bucket nodes includes a set of CPT codes, from the plurality of CPT codes, that are semantically related.

5. The computer-implemented method of claim 1, wherein the plurality of heterogenous aggregators of the graph convolutional neural network-based model include:
   a patient aggregator configured to learn relatedness between the plurality of patient nodes;
   a bucket aggregator configured to learn relatedness between the plurality of bucket nodes; and a CPT aggregator configured to learn relatedness between the plurality of procedure code nodes.

6. The computer-implemented method of claim 1, wherein at least one known procedure from the one or more known procedures included in the plurality of known care paths is part of a treatment plan for medical conditions of the plurality of patients, and wherein the one or more procedures identified and included in the personalized care path are to be performed with respect to the new patient to treat a medical condition of the new patient.

7. The computer-implemented method of claim 1, wherein the demographic data includes at least one of: age information, gender information, location information, income level, education level, household data, ethnic origin, employment data, marital status, children data, or languages spoken.

8. The computer-implemented method of claim 1, wherein the medical data includes at least one of: health condition, claim information, medication information, hospitalization information, lab information, or procedures information.

9. The computer-implemented method of claim 1, further comprising:

causing to be displayed, by the one or more processors, at least a portion of the data associated with the personalized care path for the new patient via a graphical user interface (GUI) on the device.

10. The computer-implemented method of claim 9, wherein the at least the portion of the data associated with the personalized care path for the new patient includes at least one of:

the one or more procedures identified and included in the personalized care path;

a transaction variable, including a cost estimate, associated with the personalized care path; or a medical variable, including a duration or an intensity, associated with the personalized care path.

11. A system comprising:

one or more processors; and one or more non-transitory computer readable media storing processor-executable instructions which, when executed by the one or more processors, cause the one or more processors to perform operations comprising:

receiving a plurality of training datasets associated with a plurality of patients, the plurality of training datasets including (i) a plurality of relevant data associated with the plurality of patients including demographic data and medical data associated with the plurality of patients and (ii) a plurality of known care paths for the plurality of patients, wherein each known care path of the plurality of known care paths includes one or more known procedures, from a plurality of procedures, undergone by a respective patient;

generating, based on the plurality of training datasets, a patient-bucket-procedure (PBP) graph, the PBP graph including:

(i) a plurality of nodes comprising (a) a plurality of patient nodes representing the plurality of relevant data associated with the plurality of patients, (b) a plurality of procedure code nodes representing a plurality of procedure codes for the plurality of procedures, and (c) a plurality of bucket nodes for the plurality of patients that represent the plurality of known care paths for the plurality of patients, and (ii) a plurality of links comprising (a) first links between the plurality of bucket nodes and the plurality of patient nodes corresponding to the plurality of patients, and (b) second links between the plurality of bucket nodes and the plurality of procedure code nodes representing procedure codes for the one or more known procedures;

defining, based on a structure of the PBP graph, an architecture of a graph convolutional neural network-based model, wherein the architecture includes (i) an input layer configured to receive input data, (ii) a plurality of embedding layers configured for use with a plurality of heterogenous aggregators to learn an embedding of each node of the plurality of patient nodes, the plurality of bucket nodes, and the plurality of procedure code nodes by modeling interactive signals, and (iii) an output layer configured to generate output data based on the learned embeddings;

training, using the PBP graph and based on the plurality of training datasets, the graph convolutional neural network-based model;

receiving, via the input layer of the trained graph convolutional neural network-based model, new relevant data associated with a new patient including demographic data and medical data associated with the new patient as the input data;

identifying, via the plurality of embedding layers of the trained graph convolutional neural network-based model, (i) a patient from the plurality of patients similar to the new patient and (ii) one or more procedures represented by one of the plurality of bucket nodes corresponding to the patient;

generating, via the output layer of the trained graph convolutional neural network-based model, a personalized care path for the new patient as the output data, the personalized care path including the one or more procedures identified; and providing data associated with the personalized care path for the new patient to a device associated with a user.

12. The system of claim 11, wherein the plurality of procedure code nodes include a plurality of current procedural terminology (CPT) codes corresponding the plurality of procedures, and wherein the plurality of bucket nodes are determined by:

determining the one or more known procedures included in the plurality of known care paths, the one or more known procedures occurring during a pre-determined time period;

determining one or more of the plurality of CPT codes corresponding to the one or more known procedures; and ordering the one or more of the plurality of CPT codes chronologically within the plurality of bucket nodes based on an occurrence of the one or more known procedures during the pre-determined time period.

13. The system of claim 12, wherein each of the plurality of CPT codes is included in one or more of the plurality of bucket nodes.

14. One or more non-transitory computer readable media storing instructions that, when executed by one or more processors, cause the one or more processors to perform operations comprising:

receiving a plurality of training datasets associated with a plurality of patients, the plurality of training datasets including (i) a plurality of relevant data associated with the plurality of patients including demographic data and medical data associated with the plurality of patients and (ii) a plurality of known care paths for the plurality of patients, wherein each known care path of the plurality of known care paths includes one or more known procedures, from a plurality of procedures, undergone by a respective patient;

generating, based on the plurality of training datasets, a patient-bucket-procedure (PBP) graph, the PBP graph including:

(i) a plurality of nodes comprising (a) a plurality of patient nodes representing the plurality of relevant data associated with the plurality of patients, (b) a plurality of procedure code nodes representing a plurality of procedure codes for the plurality of procedures, and (c) a plurality of bucket nodes for the plurality of patients that represent the plurality of known care paths for the plurality of patients, and (ii) a plurality of links comprising (a) first links between the plurality of bucket nodes and the plurality of patient nodes corresponding to the plurality of patients, and (b) second links between the plurality of bucket nodes and the plurality of procedure code nodes representing procedure codes for the one or more known procedures;

defining, based on a structure of the PBP graph, an architecture of a graph convolutional neural network-based model, wherein the architecture includes (i) an input layer configured to receive input data, (ii) a plurality of embedding layers configured for use with a plurality of heterogenous aggregators to learn an embedding of each node of the plurality of patient nodes, the plurality of bucket nodes, and the plurality of procedure code nodes by modeling interactive signals, and (iii) an output layer configured to generate output data based on the learned embeddings;

training, using the PBP graph and based on the plurality of training datasets, the graph convolutional neural network-based model;

receiving, via the input layer of the trained graph convolutional neural network-based model, new relevant data associated with a new patient including demographic data and medical data associated with the new patient as the input data;

identifying, via the plurality of embedding layers of the trained graph convolutional neural network-based model, (i) a patient from the plurality of patients similar to the new patient and (ii) one or more procedures represented by one of the plurality of bucket nodes corresponding to the patient;

generating, via the output layer of the trained graph convolutional neural network-based model, a personalized care path for the new patient as the output data, the personalized care path including the one or more procedures identified; and providing data associated with the personalized care path for the new patient to a device associated with a user.

15. The computer-implemented method of claim 1, wherein the plurality of relevant data associated with the plurality of patients that is represented by the plurality of patient nodes of the PBP graph includes a plurality of variables, and the learned embeddings used by the graph convolutional neural network-based model include a learned relationship between the plurality of variables and the one or more known procedures, from the plurality of procedures, undergone by the plurality of patients.

16. The computer-implemented method of claim 1, wherein the graph convolutional neural network-based model uses the learned embeddings as a graph encoder.

17. The computer-implemented method of claim 1, further comprising:

determining, by the one or more processors, a transaction variable associated with the personalized care path based on the one or more procedures included in the personalized care path and a portion of the new relevant data associated with the new patient; and replacing, by the one or more processors, and based on the determined transaction variable, at least one of the one or more procedures in the personalized care path with an alternative procedure.

18. The computer-implemented method of claim 1, wherein modeling the interactive signals includes building, based on the PBP graph, a patient-bucket interaction matrix, a bucket-procedure code interaction matrix, and a patient-procedure code interaction matrix.

19. The computer-implemented method of claim 1, wherein the plurality of embedding layers include: a first embedding layer configured to model patient-bucket node interactive signals based on the first links, a second embedding layer configured to model bucket-procedure code node interactive signals based on the second links, and a third embedding layer configured to model patient-procedure code node interactive signals based on the first links and the second links.

20. The computer-implemented method of claim 1, wherein generating the PBP graph comprises:

for a bucket node of the plurality of bucket nodes that represents a known care path, from the plurality of known care paths, having multiple known procedures, (i) categorizing the known care path into multiple segments based on procedure characteristics and a time of occurrence of the multiple known procedures over a time period spanning the known care path, and (ii) using a natural language processing (NLP) model to build a semantic relationship between the multiple segments based on procedure code descriptions for the multiple known procedures and the time of occurrence, wherein, based on the semantic relationship built, the graph convolutional neural network-based model is trained to predict whether certain procedures occur together within a pre-defined time window of each other.

\* \* \* \* \*